(12) United States Patent
Zhang et al.

(10) Patent No.: US 12,338,441 B2
(45) Date of Patent: Jun. 24, 2025

(54) APTAMER FOR SCLEROSTIN AND USE THEREOF

(71) Applicant: APTACURE THERAPEUTICS LIMITED, Hong Kong (CN)

(72) Inventors: Ge Zhang, Hong Kong (CN); Yuanyuan Yu, Hong Kong (CN); Shuaijian Ni, Hong Kong (CN); Yixin He, Hong Kong (CN)

(73) Assignee: APTACURE THERAPEUTICS LIMITED, Hong Kong (CN)

( * ) Notice: Subject to any disclaimer, the term of this patent is extended or adjusted under 35 U.S.C. 154(b) by 870 days.

(21) Appl. No.: 16/969,314

(22) PCT Filed: Feb. 11, 2019

(86) PCT No.: PCT/CN2019/074764
§ 371 (c)(1),
(2) Date: Mar. 9, 2021

(87) PCT Pub. No.: WO2019/154410
PCT Pub. Date: Aug. 15, 2019

(65) Prior Publication Data
US 2021/0198672 A1 Jul. 1, 2021

(30) Foreign Application Priority Data
Feb. 12, 2018 (CN) .......................... 201810145662.6

(51) Int. Cl.
*C12N 15/115* (2010.01)
(52) U.S. Cl.
CPC ...... *C12N 15/115* (2013.01); *C12N 2310/315* (2013.01); *C12N 2310/322* (2013.01); *C12N 2310/344* (2013.01)

(58) Field of Classification Search
CPC ............ C12N 15/115; C12N 2310/315; C12N 2310/322; C12N 2310/344;
(Continued)

(56) References Cited

U.S. PATENT DOCUMENTS 5,780,449 A * 7/1998 Bracht ...................... A61P 7/02
435/6.12
7,868,134 B2 1/2011 Winkler et al.
(Continued)

FOREIGN PATENT DOCUMENTS

CN 103114147 B 9/2015

OTHER PUBLICATIONS

Shum KT, Chan C, Leung CM, Tanner JA. Identification of a DNA aptamer that inhibits sclerostin's antagonistic effect on Wnt signalling. Biochem J. Mar. 15, 2011;434(3):493-501. doi: 10.1042/BJ20101096. PMID: 21204783. (Year: 2011).*
(Continued)

*Primary Examiner* — Nancy J Leith
*Assistant Examiner* — Ruth Sophia Arieti
(74) *Attorney, Agent, or Firm* — Jenkins, Taylor & Hunt, P.A.

(57) ABSTRACT

The invention relates to the field of biomedicine. Specifically, the present invention relates to aptamers against sclerostin and uses thereof, especially uses in the treatment of sclerostin-related diseases such as osteoporosis.

12 Claims, 18 Drawing Sheets
Specification includes a Sequence Listing.

(58) Field of Classification Search
CPC .......... C12N 2310/16; C12N 2310/321; C12N 2310/3521; C12N 2310/3533; A61K 47/60; A61K 31/712; A61P 19/02
See application file for complete search history.

(56) References Cited

U.S. PATENT DOCUMENTS

| | | | |
|---|---|---|---|
| 8,552,166 | B2 | 10/2013 | Alexander et al. |
| 8,553,166 | B2* | 10/2013 | Liu .................. G02F 1/136286 349/46 |
| 8,877,196 | B2 | 11/2014 | Ellies |
| 10,449,250 | B2 | 10/2019 | Jiangsu |
| 2011/0294872 | A1* | 12/2011 | Tanner .................. A61P 19/10 536/23.1 |

OTHER PUBLICATIONS

Sakamoto T, Ennifar E, Nakamura Y. Thermodynamic study of aptamers binding to their target proteins. Biochimie. Feb. 2018;145:91-97. doi: 10.1016/j.biochi.2017.10.010. Epub Oct. 18, 2017. PMID: 29054802. (Year: 2017).*
Neubig RR, Spedding M, Kenakin T, Christopoulos A; International Union of Pharmacology Committee on Receptor Nomenclature and Drug Classification. International Union of Pharmacology Committee on Receptor Nomenclature and Drug Classification. XXXVIII. (Year: 2003).*
U.S. Appl. No. 18/283,468, filed Sep. 2023.*
Yu et al. 2016. Molecular Selection, Modification and Development of Therapeutic Oligonucleotide Aptamers. Int. J. Mol. Sci. 17:358 (Year: 2016).*
Lyu. 2017. Therapeutic potential of nucleic acid aptamers against sclerostin in the treatment of osteoporosis. Masters Thesis, Hong Kong Baptist University. Awarded Aug. 21, 2017 (Year: 2017).*
Lewiecki (2014. Role of sclerostin in bone and cartilage and its potential as a therapeutic target in bone diseases. Ther. Adv. Musculoskel. Dis. 6[2]:48-57) (Year: 2014).*
Bouaziz (2014. 594. Lack of Sclerostin Promotes Osteoarthritis By Activating Canonical and Non-Canonical Wnt P)ts Osteoarthritis Cartilage 22:S57-S489 (Year: 2014).*
Ren (et al. 2016. Sclerostin antibody [Scl-Ab] improves osteomalacia phenotype in dentin matrix protein 1 [Dmp1] knockout mice with little impact on serum levels of phosphorus and FGF23. Matrix Biol. 52-54:151-161) (Year: 2016).*
Wehmeyer (et al. 2016. Sclerostin inhibition promotes TNF-dependent inflammatory joint destruction. Sci. Translat. Med 8[330]:330ra350) (Year: 2016).*
Sebastian (and Loots. 2017. Genetics of Sost/SOST in sclerosteosis and van Buchem disease animal models. Metabolism 80:37-47) (Year: 2017).*
Wikipedia (2017. "Osteopenia". Available at Wikipedia.org. Accessed on Nov. 15, 2024) (Year: 2017).*
McDonald (et al. 2017. Inhibiting the osteocyte-specific protein sclerostin increases bone mass and fracture resistance in multiple myeloma. Blood 129[26]:3452-3464) (Year: 2017).*
Sinder (et al. 2019. Effect of anti-sclerostin therapy and osteogenesis imperfecta on tissue-level properties in growing and adult mice while controlling for tissue age. Bone 84:222-229) (Year: 2019).*
International Search Report for PCT International Patent Application Serial No. PCT/CN2019/074764 dated May 8, 2019.
Padhi et al. (2011). "Single-dose, placebo-controlled, randomized study of AMG 785, a sclerostin monoclonal antibody." J. Bone Miner. Res. 26(1):19-26.
Shum et al. (2011) Identification of a DNA aptamer that inhibits sclerostin's antagonistic effect on Wnt signalling. Biochemical Journal 434(3):493-501.
Written Opinion of the International Searching Authority corresponding to International Patent Application No. PCT/CN2019/074764 dated Aug. 15, 2019.

* cited by examiner

SEQUENCE LISTING

```
<160> NUMBER OF SEQ ID NOS: 29

<210> SEQ ID NO 1
<211> LENGTH: 40
<212> TYPE: DNA
<213> ORGANISM: Artificial Sequence
<220> FEATURE:
<223> OTHER INFORMATION: aptscl56
```

<400> SEQUENCE: 1
cggggtgtgg gttcgtcgtt agcttgattt ggcagctgcc                                40

<210> SEQ ID NO 2
<211> LENGTH: 42
<212> TYPE: DNA
<213> ORGANISM: Artificial Sequence
<220> FEATURE:
<223> OTHER INFORMATION: aptscl132

<400> SEQUENCE: 2
cccagacgag acacctcatg cttttccccg ggggaggggt at                            42

<210> SEQ ID NO 3
<211> LENGTH: 76
<212> TYPE: DNA
<213> ORGANISM: Artificial Sequence
<220> FEATURE:
<223> OTHER INFORMATION: aptscl6

<400> SEQUENCE: 3
cgtacggtcg acgctagctg aagggtggg ggcgggggt cctcgcctcg aacgtacgca           60
cgtggagctc ggatcc                                                         76

<210> SEQ ID NO 4
<211> LENGTH: 76
<212> TYPE: DNA
<213> ORGANISM: Artificial Sequence
<220> FEATURE:
<223> OTHER INFORMATION: aptscl9

<400> SEQUENCE: 4
cgtacggtcg acgctagctg ggggtagggg gaccctggct agttagtcac cgtttcgaca         60
cgtggagctc ggatcc                                                         76

<210> SEQ ID NO 5
<211> LENGTH: 76
<212> TYPE: DNA
<213> ORGANISM: Artificial Sequence
<220> FEATURE:
<223> OTHER INFORMATION: aptscl15

<400> SEQUENCE: 5
cgtacggtcg acgctagcga gggggccaac tatgcttagt gggggggttg accgtatcca         60
cgtggagctc ggatcc                                                         76

<210> SEQ ID NO 6
<211> LENGTH: 76
<212> TYPE: DNA
<213> ORGANISM: Artificial Sequence
<220> FEATURE:
<223> OTHER INFORMATION: aptscl46

<400> SEQUENCE: 6
cgtacggtcg acgctagcgg gtggattaag ggggccccgt ctgtaggcga ttggcgaaca         60
cgtggagctc ggatcc                                                         76

<210> SEQ ID NO 7
<211> LENGTH: 76
<212> TYPE: DNA
<213> ORGANISM: Artificial Sequence
<220> FEATURE:

```
<223> OTHER INFORMATION: aptscl51

<400> SEQUENCE: 7
cgtacggtcg acgctagctg ggggtagggg gtccttggct acggtgattc ggatgtgaca      60
cgtggagctc ggatcc                                                     76

<210> SEQ ID NO 8
<211> LENGTH: 56
<212> TYPE: DNA
<213> ORGANISM: Artificial Sequence
<220> FEATURE:
<223> OTHER INFORMATION: aptscl1

<400> SEQUENCE: 8
cgtacggtcg acgctagctc ttgttcatcg atcctacgca cgtggagctc ggatcc          56

<210> SEQ ID NO 9
<211> LENGTH: 54
<212> TYPE: DNA
<213> ORGANISM: Artificial Sequence
<220> FEATURE:
<223> OTHER INFORMATION: aptscl2

<400> SEQUENCE: 9
cgtacggtcg acgctagcca gccaaagaca gagatgcacg tggagctcgg atcc            54

<210> SEQ ID NO 10
<211> LENGTH: 55
<212> TYPE: DNA
<213> ORGANISM: Artificial Sequence
<220> FEATURE:
<223> OTHER INFORMATION: aptscl3

<400> SEQUENCE: 10
cgtacggtcg acgctagctg ttgtacatcg ccttacgcac gtggagctcg gatcc           55

<210> SEQ ID NO 11
<211> LENGTH: 56
<212> TYPE: DNA
<213> ORGANISM: Artificial Sequence
<220> FEATURE:
<223> OTHER INFORMATION: aptscl5

<400> SEQUENCE: 11
cgtacggtcg acgctagctg ttgttcatcg acttgacgca cgtggagctc ggatcc          56

<210> SEQ ID NO 12
<211> LENGTH: 51
<212> TYPE: DNA
<213> ORGANISM: Artificial Sequence
<220> FEATURE:
<223> OTHER INFORMATION: aptscl8

<400> SEQUENCE: 12
cgtacggtcg acgctagccg gcgaaattgc taccacgtgg agctcggatc c               51

<210> SEQ ID NO 13
<211> LENGTH: 52
<212> TYPE: DNA
<213> ORGANISM: Artificial Sequence
<220> FEATURE:
<223> OTHER INFORMATION: aptscl12

<400> SEQUENCE: 13
cgtacggtcg acgctagccg ttgactcgtt gctacacgtg gagctcggat cc              52
```

<210> SEQ ID NO 14
<211> LENGTH: 55
<212> TYPE: DNA
<213> ORGANISM: Artificial Sequence
<220> FEATURE:
<223> OTHER INFORMATION: aptscl16

<400> SEQUENCE: 14
cgtacggtcg acgctagctg gtttcatcga tcgtatccac gtggagctcg gatcc        55

<210> SEQ ID NO 15
<211> LENGTH: 55
<212> TYPE: DNA
<213> ORGANISM: Artificial Sequence
<220> FEATURE:
<223> OTHER INFORMATION: aptscl22

<400> SEQUENCE: 15
cgtacggtcg acgctagctg ggtttatcga ctagttccac gtggagctcg gatcc        55

<210> SEQ ID NO 16
<211> LENGTH: 51
<212> TYPE: DNA
<213> ORGANISM: Artificial Sequence
<220> FEATURE:
<223> OTHER INFORMATION: aptscl29

<400> SEQUENCE: 16
cgtacggtcg acgctagccg gagacctgag gttcacgtgg agctcggatc c            51

<210> SEQ ID NO 17
<211> LENGTH: 56
<212> TYPE: DNA
<213> ORGANISM: Artificial Sequence
<220> FEATURE:
<223> OTHER INFORMATION: aptscl32

<400> SEQUENCE: 17
cgtacggtcg acgctagctg tgttaatcgc cgtacctcca cgtggagctc ggatcc       56

<210> SEQ ID NO 18
<211> LENGTH: 190
<212> TYPE: PRT
<213> ORGANISM: Homo sapiens

<400> SEQUENCE: 18

Gln Gly Trp Gln Ala Phe Lys Asn Asp Ala Thr Glu Ile Ile Pro Glu
1               5                   10                  15

Leu Gly Glu Tyr Pro Glu Pro Pro Pro Glu Leu Glu Asn Asn Lys Thr
            20                  25                  30

Met Asn Arg Ala Glu Asn Gly Gly Arg Pro Pro His His Pro Phe Glu
        35                  40                  45

Thr Lys Asp Val Ser Glu Tyr Ser Cys Arg Glu Leu His Phe Thr Arg
    50                  55                  60

Tyr Val Thr Asp Gly Pro Cys Arg Ser Ala Lys Pro Val Thr Glu Leu
65                  70                  75                  80

Val Cys Ser Gly Gln Cys Gly Pro Ala Arg Leu Leu Pro Asn Ala Ile
                85                  90                  95

Gly Arg Gly Lys Trp Trp Arg Pro Ser Gly Pro Asp Phe Arg Cys Ile
            100                 105                 110

Pro Asp Arg Tyr Arg Ala Gln Arg Val Gln Leu Leu Cys Pro Gly Gly
            115                 120                 125

Glu Ala Pro Arg Ala Arg Lys Val Arg Leu Val Ala Ser Cys Lys Cys
        130                 135                 140

Lys Arg Leu Thr Arg Phe His Asn Gln Ser Glu Leu Lys Asp Phe Gly
145                 150                 155                 160

Thr Glu Ala Ala Arg Pro Gln Lys Gly Arg Lys Pro Arg Pro Arg Ala
                165                 170                 175

Arg Ser Ala Lys Ala Asn Gln Ala Glu Leu Glu Asn Ala Tyr
            180                 185                 190

<210> SEQ ID NO 19
<211> LENGTH: 49
<212> TYPE: DNA
<213> ORGANISM: Artificial Sequence
<220> FEATURE:
<223> OTHER INFORMATION: aptscl3-1

<400> SEQUENCE: 19
gtcgacgcta gctgttgtac atcgccttac gcacgtggag ctcggatcc          49

<210> SEQ ID NO 20
<211> LENGTH: 49
<212> TYPE: DNA
<213> ORGANISM: Artificial Sequence
<220> FEATURE:
<223> OTHER INFORMATION: aptscl3-2

<400> SEQUENCE: 20
cgtacggtcg acgctagctg ttgtacatcg ccttacgcac gtggagctc          49

<210> SEQ ID NO 21
<211> LENGTH: 37
<212> TYPE: DNA
<213> ORGANISM: Artificial Sequence
<220> FEATURE:
<223> OTHER INFORMATION: aptscl3-3

<400> SEQUENCE: 21
gctagctgtt gtacatcgcc ttacgcacgt ggagctc                       37

<210> SEQ ID NO 22
<211> LENGTH: 37
<212> TYPE: DNA
<213> ORGANISM: Artificial Sequence
<220> FEATURE:
<223> OTHER INFORMATION: aptscl3-4

<400> SEQUENCE: 22
gtcgacgcta gctgttgtac atcgccttac gcacgtg                       37

<210> SEQ ID NO 23
<211> LENGTH: 31
<212> TYPE: DNA
<213> ORGANISM: Artificial Sequence
<220> FEATURE:
<223> OTHER INFORMATION: aptscl3-5

<400> SEQUENCE: 23
gctagctgtt gtacatcgcc ttacgcacgt g                             31

<210> SEQ ID NO 24
<211> LENGTH: 25
<212> TYPE: DNA

```
<213> ORGANISM: Artificial Sequence
<220> FEATURE:
<223> OTHER INFORMATION: aptscl3-6

<400> SEQUENCE: 24
tgttgtacat cgccttacgc acgtg                                          25

<210> SEQ ID NO 25
<211> LENGTH: 40
<212> TYPE: DNA
<213> ORGANISM: Artificial Sequence
<220> FEATURE:
<223> OTHER INFORMATION: Random sequence

<400> SEQUENCE: 25
atgcaagcac attgtgatcg cttcaaatgt cttccgtccg                          40

<210> SEQ ID NO 26
<211> LENGTH: 76
<212> TYPE: DNA
<213> ORGANISM: Artificial Sequence
<220> FEATURE:
<223> OTHER INFORMATION: long ssDNA library
<220> FEATURE:
<221> NAME/KEY: misc_feature
<222> LOCATION: (19)..(58)
<223> OTHER INFORMATION: n is a, c, g, or t

<400> SEQUENCE: 26
cgtacggtcg acgctagcnn nnnnnnnnnn nnnnnnnnnn nnnnnnnnca               60
cgtggagctc ggatcc                                                    76

<210> SEQ ID NO 27
<211> LENGTH: 61
<212> TYPE: DNA
<213> ORGANISM: Artificial Sequence
<220> FEATURE:
<223> OTHER INFORMATION: short ssDNA
<220> FEATURE:
<221> NAME/KEY: misc_feature
<222> LOCATION: (19)..(43)
<223> OTHER INFORMATION: n is a, c, g, or t

<400> SEQUENCE: 27
cgtacggtcg acgctagcnn nnnnnnnnnn nnnnnnnnn nnncacgtgg agctcggatc    60
c                                                                    61

<210> SEQ ID NO 28
<211> LENGTH: 18
<212> TYPE: DNA
<213> ORGANISM: Artificial Sequence
<220> FEATURE:
<223> OTHER INFORMATION: forward primer

<400> SEQUENCE: 28
cgtacggtcg acgctagc                                                  18

<210> SEQ ID NO 29
<211> LENGTH: 18
<212> TYPE: DNA
<213> ORGANISM: Artificial Sequence
<220> FEATURE:
<223> OTHER INFORMATION: reverse primer

<400> SEQUENCE: 29
ggatccgagc tccacgtg                                                  18
```

APTAMER FOR SCLEROSTIN AND USE THEREOF

TECHNICAL FIELD

The invention relates to the field of biomedicine. Specifically, the present invention relates to aptamers against sclerostin and uses thereof, especially uses in the treatment of sclerostin-related diseases such as osteoporosis.

BACKGROUND OF THE INVENTION

Osteoporosis is a disease with reduced bone mass and bone strength, leading to an increased risk of bone fractures (Hamersma, Gardner et al. 2003). A variety of drugs for osteoporosis treatment are mainly anti-resorptive agents, which inhibit bone resorption to prevent further bone loss (Russell, Watts et al. 2008, Pennypacker, Duong et al. 2011). Parathyroid hormone (PTH) peptide is the only available anabolic agent for stimulating bone formation to reverse established osteoporosis (Compston 2007, Greenspan, Bone et al. 2007). Unfortunately, long term treatment using PTH leads to risk of osteosarcoma (Whitfield 2001, Orwoll, Scheele et al. 2003). Therefore, alternative anabolic drugs which can promote bone formation without any adverse effects are seriously needed.

Sclerostin is a promising target for developing therapeutics in established osteoporosis (Rey and Ellies 2010). Humanized monoclonal antibody against human sclerostin has been reported to promote bone formation and increase bone mass with good tolerance in clinical trials. However, there are several major concerns for therapeutic antibodies, including high immunogenicity (Padhi, Jang et al. 2011, Padhi, Allison et al. 2014), expensive and laborious to produce (Baker 2015, Bradbury and Pluckthun 2015, Groff, Brown et al. 2015), unstable which requires a continuous cold chain for transportation and storage (Jayasena 1999). Therefore, an alternative anti-sclerostin agent with no immunogenicity, easy production, low cost and high stability is desirable for bone anabolic therapy.

Aptamers are short single-stranded oligonucleotides which bind to their targets through conformational complementarity (Ellington and Szostak 1990, Tuerk and Gold 1990). Aptamers can be tailored selected against positive and negative targets. Compared to therapeutic antibodies, aptamers possess similar affinity and specificity, but have some important advantages. For immunogenicity, aptamers are not recognized by the immune system as foreign and do not stimulate a negative immune response because of the small size (Keefe, Pai et al. 2010). For production and cost, aptamers are identified in vitro under various selection conditions and can be easily synthesized by chemical methods, so production is less expensive and less risky (Banerjee 2010). For stability, aptamers have an indefinite shelf life as they are temperature resistant and can tolerate transportation without any special requirements for cooling, eliminating the need for a continuous cold chain (Jayasena 1999). Pegaptanib, an aptamer against vascular endothelial growth factor (VEGF) for the treatment of age-related macular degeneration has been successfully used in clinic (Jellinek, Green et al. 1994, Ruckman, Green et al. 1998, Ng and Adamis 2006, Que-Gewirth and Sullenger 2007).

Therefore, it is desired to develop aptamers against sclerostin to replace monoclonal antibodies for the treatment of osteoporosis.

SUMMARY OF THE INVENTION

In one aspect, the present invention provides an aptamer against sclerostin, wherein the aptamer
 i) comprises a nucleotide sequence having at least about 90%, at least about 91%, at least about 92%, at least about 93%, at least about 94% or at least about 95% identity with any one of SEQ ID NOs: 1-17, or
 ii) comprises at least 30, at least 35, at least 40, at least 45, at least 50 or more contiguous nucleotides within any one of SEQ ID NOs: 1-17,
 preferably, the aptamer comprises a sequence of any one of SEQ ID NOs: 1-17 or 19-24,
 wherein the aptamer specifically binds to sclerostin.

In some embodiments, the aptamer has a $K_d$ to sclerostin of less than 100 nM, preferably less than 50 nM, preferably less than 40 nM, preferably less than 30 nM, preferably less than 20 nM, preferably less than 10 nM or less.

In some embodiments, the aptamer is capable of inhibiting the biological activity of sclerostin. In some embodiments, the aptamer can block the antagonistic effect of sclerostin in a cell-based Wnt signaling assay. In some embodiments, the aptamer has an EC50 value of less than 100 µg/ml, preferably less than 50 µg/ml, preferably less than 40 µg/ml, preferably less than 30 µg/ml, preferably less than 20 µg/ml, preferably less than 10 µg/ml or less for inhibiting the biological activity of sclerostin, for example, inhibiting the antagonistic effect of sclerostin on Wnt signaling pathway.

In some embodiments, the aptamer further comprises one or more modifications that confer enhanced nuclease resistance to the aptamer and/or enhance the in vivo half-life of the aptamer. In some embodiments, the modification includes a 3' inverted deoxythymidine (3' idT) modification. In some embodiments, the modification includes substituting one or more naturally occurring nucleotides with modified nucleotides selected from the group consisting of 2'-fluoro, 2'-methoxyethyl, 2'-methoxy or 2' allyloxy modified nucleotides, preferably 2'-methoxy modified nucleotides. In some embodiments, the modification includes an internucleotide modification, such as an internucleotide phosphorothioate bond modification. In some embodiments, the modification includes PEG modification. In some embodiments, the aptamer comprises 2'-methoxy (2'-OMe) modification, 3' inverse deoxythymidine (3' idT) modification and/or PEG modification.

In another aspect, the present invention provides a method for treating sclerostin-related diseases, the method comprises administering a therapeutically effective amount of the aptamer against sclerostin of the present invention to a subject in need thereof, for example, the subject is a human.

In some embodiments, the sclerostin-related disease is selected from osteoporosis, osteopenia, osteomalacia, osteogenesis imperfecta (OI), ischemic osteonecrosis, rheumatoid arthritis, fracture, osteoarthritis and myeloma.

In another aspect, the present invention provides a pharmaceutical composition comprising at least one aptamer against sclerostin of the present invention, and a pharmaceutically acceptable carrier or excipient.

In another aspect, the present invention provides the use of the aptamer against sclerostin of the present invention or the pharmaceutical composition of the present invention in the preparation of a medicine for treating sclerostin-related diseases.

In some embodiments, the sclerostin-related disease is selected from osteoporosis, osteopenia, osteomalacia, osteogenesis imperfecta (OI), ischemic osteonecrosis, rheumatoid arthritis, fracture, osteoarthritis and myeloma.

Figure 1A:
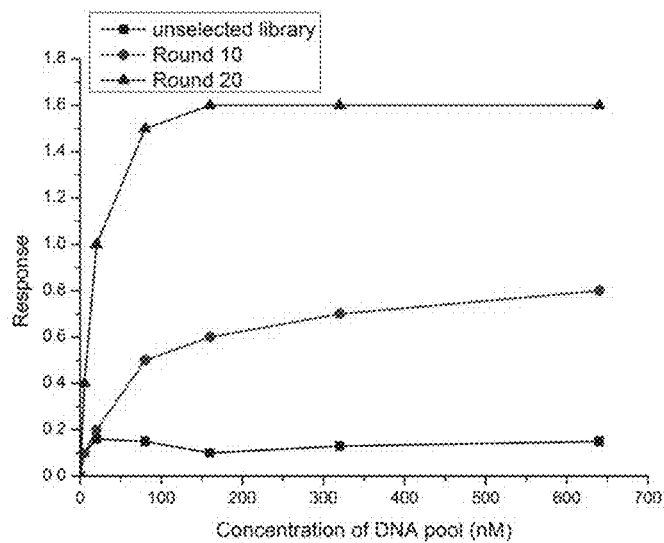
FIG. 1. The enrichment of high affinity aptamers against sclerostin through SELEX. (A) The binding affinity of the enriched ssDNA and unselected library to sclerostin. (B) The binding affinity of the enriched ssDNA library and unselected library to control proteins.

(SEQ ID NO: 25)
5'-ATGCAAGCACATTGTGATCGCTTCAAATGTCTTCCGTCCG-3'.

The data are expressed as mean±standard deviation and OVX–BS. n=10 for each group. *P<0.05; P<0.01; *P<0.005; ****P<0.0001.

DETAILED DESCRIPTION OF THE INVENTION

Unless indicated or defined otherwise, all terms used have their usual meaning in the art, which will be clear to the skilled person. Reference is for example made to the standard handbooks, such as Sambrook et al, "Molecular Cloning: A Laboratory Manual"; Lewin, "Genes IV"; and Roitt et al., "Immunology" (8th Ed.), as well as to the general background art cited herein. Furthermore, unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

Definitions

As used herein, the term "nucleotide" refers to a ribonucleotide or a deoxyribonucleotide, or a modified form thereof, as well as an analog thereof. Nucleotides include species that include purines (e.g., adenine, hypoxanthine, guanine, and their derivatives and analogs) as well as pyrimidines (e.g., cytosine, uracil, thymine, and their derivatives and analogs).

As used herein, "nucleic acid," "oligonucleotide," and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included. The terms "polynucleotide," "oligonucleotide," and "nucleic acid" include double- or single-stranded molecules. Nucleic acid, oligonucleotide, and polynucleotide are broader terms than the term aptamer and, thus, the terms nucleic acid, oligonucleotide, and polynucleotide include aptamers but are not limited to aptamers.

As used herein, "aptamer" refers to a non-naturally occurring nucleic acid that has a desirable action on a target molecule. A desirable action includes, but is not limited to, binding of the target, catalytically changing the target, reacting with the target in a way that modifies or alters the target or the functional activity of the target, covalently attaching to the target, and facilitating the reaction between the target and another molecule. In one embodiment, the action is specific binding affinity for a target molecule (such as, sclerostin), such target molecule being a three dimensional chemical structure other than a polynucleotide that binds to the nucleic acid ligand through a mechanism which is independent of Watson/Crick base pairing or triple helix formation, wherein the aptamer is not a nucleic acid having the known physiological function of being bound by the target molecule. In this context, the "specific binding affinity" of an aptamer for its target (such as, sclerostin) means that the aptamer binds to its target generally with a much higher degree of affinity than it binds to other, non-target, components in a mixture or sample.

Sequence "identity" has an art-recognized meaning and the percentage of sequence identity between two nucleic acid or polypeptide molecules or regions can be calculated using published techniques. Sequence identity can be measured along the full length of a polynucleotide or polypeptide or along a region of the molecule. (See, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two polynucleotide or polypeptides, the term "identity" is well known to skilled artisans (Carrillo, H. & Lipman, D., SIAM J Applied Math 48:1073 (1988)). One example of an algorithm that is suitable for determining percent sequence identity is the algorithm used in the basic local alignment search tool (hereinafter "BLAST"), see, e.g. Altschul et al, J. Mol. Biol. 215:403-410, 1990 and Altschul et al, Nucleic Acids Res., 15:3389-3402, 1997. Software for performing BLAST analyses is publicly available through the National Center for Biotechnology Information (hereinafter "NCBI"). The default parameters used in determining sequence identity using the software available from NCBI, e.g., BLASTN (for nucleotide sequences) are described in McGinnis et al, Nucleic Acids Res., 32: W20-W25, 2004.

Aptamers Against Sclerostin

Based on the protein-SELEX technology, the present inventors used sclerostin as the target protein for positive screening and unrelated proteins for negative screening, and finally selected aptamers that specifically bind to sclerostin with high affinity. The sclerostin described herein is preferably human sclerostin, for example, the sclerostin whose amino acid sequence is shown in SEQ ID NO:18.

Exemplary human sclerostin amino acid sequence:

```
                                            (SEQ ID NO: 18)
QGWQAFKNDATEIIPELGEYPEPPPELENNKTMNRAENGGRPPHHPFET

KDVSEYSCRELHFTRYVTDGPCRSAKPVTELVCSGQCGPARLLPNAIGR

GKWWRPSGPDFRCIPDRYRAQRVQLLCPGGEAPRARKVRLVASCKCKRL

TRFHNQSELKDFGTEAARPQKGRKPRPRARSAKANQAELENAY
```

Therefore, in one aspect, the present invention provides an aptamer against sclerostin, the aptamer comprises a nucleotide sequence having at least about 90% identity, at least about 91% identity, at least about 90% identity, about 92% identity, at least about 93% identity, at least about 94% identity, at least about 95% identity, at least about 96% identity, at least about 97% identity, at least about 98% identity, or at least about 99% identity to any one of SEQ ID NOs: 1-17, or the aptamer comprises at least 30, at least 35, at least 40, at least 45, at least 50, or more consecutive nucleotides within any one of SEQ ID NOs: 1-17. In some embodiments, the aptamer specifically binds to sclerostin. In some preferred embodiments, the aptamer comprises a nucleotide sequence of any one of SEQ ID NOs: 1-17 and 19-24, and more preferably, the aptamer comprises a nucleotide sequence of any one of SEQ ID NOs: 1, 3, 10 or 19-23.

In some embodiments, the aptamer of the present invention has a Kd (dissociation constant) to sclerostin of less than 100 nM, preferably less than 50 nM, preferably less than 40 nM, preferably less than 30 nM, preferably less than 20 nM, preferably less than 10 nM or less. The Kd is measured, for example, by enzyme-linked oligonucleotide assay (ELONA).

In some embodiments, the aptamer of the present invention inhibits the biological activity of sclerostin. "Inhibition" means that the biological activity of sclerostin is reduced in the presence of the aptamer compared with the absence of the aptamer, for example, reduced by at least about 10%, at least about 20%, at least about 30%, at least about 40%, at least about 50%, at least about 60%, at least about 70%, at least about 80%, even at least about 90%.

As used herein, the term "biological activity" refers to an effect on one or more cellular or extracellular processes, which can affect physiological or pathophysiological processes. The biological activities of sclerostin include, but are not limited to, antagonizing the Wnt signaling pathway.

In some embodiments, the aptamer of the present invention can inhibit the antagonistic effect of sclerostin on the Wnt signaling pathway. For example, the aptamer of the present invention can block the antagonistic effect of sclerostin in a cell-based Wnt signaling assay.

In some embodiments, the aptamer of the present invention inhibits the biological activity of sclerostin, such as inhibits the antagonistic effect of sclerostin on the Wnt signaling pathway with a EC50 value of less than 100 µg/ml, preferably less than 50 µg/ml, preferably less than 40 µg/ml, preferably less than 30 µg/ml, preferably less than 20 µg/ml, preferably less than 10 µg/ml or less. In some embodiments, the EC50 value is determined in vitro by a TOP-Wnt-induced luciferase reporter gene assay in osteoblasts.

In some embodiments, the aptamer of the present invention may also include one or more modifications. For example, the modification is a modification that confers enhanced nuclease resistance to the aptamer and/or enhances the in vivo half-life of the aptamer.

The modification includes, for example, 3' and 5' modification, such as 3' and 5' capping. In some embodiments, the aptamer is capped with inverted deoxythymidine at the 3' end, that is, a 3' inverted deoxythymidine (3' idT) modification.

The modification may also include the substitution of one or more naturally occurring nucleotides with modified nucleotides. For example, the modified nucleotides include, but are not limited to, 2'-fluoro, 2'-methoxyethyl, 2'-methoxy and/or 2' allyloxy modified nucleotides (i.e., the 2'-position hydroxyl group of the ribose is substituted by fluorine, methoxyethyl, methoxy or allyloxy, etc.). The modified nucleotides may also include C-5 modified pyrimidines. The term "C-5 modified pyrimidine" refers to a pyrimidine with a modification at the C-5 position. C-5 modified pyrimidines can enhance the nuclease resistance of oligonucleotides, and are known in the art. For example, reference can be made to PCT Application WO 2011/130195 and references cited therein. In some preferred embodiments, the modification is a 2'-methoxy (2'-OMe) modification. In some embodiments, the modification, such as 2'-methoxy (2'-OMe) modification, is made to one or more nucleotides, for example 4 nucleotides, at the 5' and/or 3' end of the aptamer.

The modifications also include internucleotide modifications, such as those internucleotide modifications with uncharged bonds (such as methyl phosphonate, phosphotriester, phosphoamine ester, carbamate, etc.) and those internucleotide modifications with charged bonds (such as phosphorothioate, phosphorodithioate, etc.), internucleotide modifications with intercalating agents (such as acridine, psoralen, etc.), internucleotide modifications containing chelating agents (such as metals, radioactive metals, boron, oxidizing metals, etc.), internucleotide modifications containing alkylating agents, and internucleotide modifications with modified bonds (for example, alpha anomeric nucleic acid, etc.).

The modification may also include pegylation modification (PEG modification). Conjugation with PEG can extend the half-life of the aptamer, such as the in vivo half-life. In some embodiments, the molecular weight of the PEG is about 1 kDa to about 100 kDa, for example, about 10 kDa to about 80 kDa, about 20 kDa to about 60 kDa, about 30 kDa to about 50 kDa, about 40 kDa. In some embodiments, the PEG may be conjugated to the 5' end of the aptamer. In some embodiments, the PEG may be conjugated to the 3' end of the aptamer.

In some embodiments, the aptamer may comprise a combination of various modifications described above. For example, the aptamer may include 2'-methoxy (2'-OMe) modification, 3' inverted deoxythymidine (3' idT) modification and/or PEG modification. Preferably, the molecular weight of the PEG is about 40 kDa.

Treatment of Diseases

In another aspect, the present invention provides a method for treating diseases by the aptamer against sclerostin of the present invention, the method comprises administering a therapeutically effective amount of the aptamer against sclerostin of the present invention to a subject in need thereof.

The diseases treated by the aptamer against sclerostin of the present invention are, for example, sclerostin-related diseases, such as sclerostin-mediated diseases.

As used herein, "a sclerostin-related disease" includes diseases in which bone mineral density (BMD) is abnormally and/or pathologically low relative to healthy subjects. Diseases characterized by low BMD and/or bone fragility include but are not limited to primary and secondary osteoporosis, osteopenia, osteomalacia, osteogenesis imperfecta (OI), avascular necrosis (osteonecrosis), fractures and implant healing (dental implants and hip implants), bone loss due to other diseases (e.g., associated with HIV infection, cancers, or arthritis). Other "sclerostin-related diseases" include but are not limited to rheumatoid arthritis, osteoarthritis, arthritis, and osteolytic lesions.

As used herein, "a sclerostin-related disease" includes sclerostin-related cancers, such as myeloma (e.g., multiple myeloma with osteolytic lesions), breast cancer, colon cancer, melanoma, hepatocellular cancer, epithelial cancer, esophageal cancer, brain cancer, lung cancer, prostate cancer, or pancreatic cancer, as well as any metastases thereof.

A "sclerostin-related disease" can also include renal and cardiovascular conditions, due at least to sclerostin's expression in the kidney and cardiovasculature. Said diseases include but are not limited to such renal disorders as glomerular diseases (e.g., acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, polycystic kidney disease, neoplasia, sickle cell disease, and chronic inflammatory diseases), tubular diseases (e.g., acute tubular necrosis and acute renal failure, polycystic renal disease medullary sponge kidney, medullary cystic disease, nephrogenic diabetes, and renal tubular acidosis), tubulointerstitial diseases (e.g., pyelonephritis, drug and toxin induced tubulointerstitial nephritis, hypercalcemic nephropathy, and hypokalemic nephropathy) acute and rapidly progressive renal failure, chronic renal failure, nephrolithiasis, gout, vascular diseases (e.g., hypertension and nephrosclerosis, microangiopathic hemolytic anemia, atheroembolic renal disease, diffuse cortical necrosis, and renal infarcts), or tumors (e.g., renal cell carcinoma and nephroblastoma).

Said diseases also include but are not limited to such cardiovascular disorders as ischemic heart disease (e.g., angina pectoris, myocardial infarction, and chronic ischemic heart disease), hypertensive heart disease, pulmonary heart disease, valvular heart disease (e.g., rheumatic fever and rheumatic heart disease, endocarditis, mitral valve prolapse, and aortic valve stenosis), congenital heart disease (e.g., valvular and vascular obstructive lesions, atrial or ventricular septal defect, and patent ductus arteriosus), or myocardial disease (e.g., myocarditis, congestive cardiomyopathy, and hypertrophic cardiomyopathy).

The subject can be any animal (domesticated, domestic animal or wild), including but not limited to cats, dogs, horses, pigs, and cows, and human subjects are preferred. As used herein, the terms patient, individual, and subject can be used interchangeably.

The subject can be a male or a female. Preferably, the human subject is at risk of fracture, more preferably the human subject is at risk of osteoporosis or suffers from osteoporosis. The human subject is preferably a female, and more preferably a female at risk of post-menopausal osteoporosis or suffering from post-menopausal osteoporosis. It is expected that the method of the present invention can be beneficial to subjects at any stage of osteoporosis.

As used herein, "treating" an individual suffering from a disease or disease condition means that the individual's symptoms are partially or completely alleviated, or remain unchanged after treatment. Thus, treatment includes prevention, treatment and/or cure. Prevention refers to prevention of a potential disease and/or prevention of worsening of symptoms or disease progression.

As used herein, "therapeutically effective amount" or "therapeutically effective dose" refers to an amount of a substance, compound, material, or composition comprising a compound that is at least sufficient to produce a therapeutic effect after administration to a subject. Thus, it is the amount necessary to prevent, cure, ameliorate, arrest or partially arrest the symptoms of the disease or condition. As used herein, "therapeutic effect" means an effect resulting from treatment of an individual that alters, generally ameliorates or alleviates the symptoms of the disease or disease condition, or cures the disease or disease condition.

The dosage regimen of the aptamer against sclerostin is selected according to a variety of factors, including, for example, the type, species, age, weight, gender, and medical condition of the patient; the severity of the condition to be treated; the route of administration; the kidney function and liver function of the patient; and the specific aptamer against sclerostin or salt thereof as used. Ordinary skilled doctors can easily determine and specify the effective amount of the composition required to prevent, combat, or inhibit the progression of the condition.

Typically, the dosage regimen of the aptamer against sclerostin is about 1 µg/kg body weight to about 100 mg/kg body weight per day.

An exemplary treatment regime entails administration once daily, once every two days, once per week, twice per week, once every two weeks, once every three weeks, once every four weeks, once a month, once every 3 months or once every three to 6 months, or with a short administration interval at the beginning (such as once per week to once every three weeks), and then an extended interval later (such as once a month to once every three to 6 months). The frequency and interval of administration can be determined by those skilled in the art according to the pharmacokinetic parameters of the aptamer.

Pharmaceutical Composition

In another aspect, the present invention also provides a pharmaceutical composition comprising at least one aptamer against sclerostin of the present invention, and a pharmaceutically acceptable carrier or excipient. Said pharmaceutical composition is used for treating, for example, sclerostin-related diseases.

The aptamers described herein can be utilized in any pharmaceutically acceptable dosage form, including but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the aptamers described herein can be formulated: (a) for administration selected from any of oral, pulmonary, intravenous, intra-arterial, intrathecal, intraarticular, rectal, ophthalmic, colonic, parenteral, intracisternal, intravaginal, intraperitoneal, local, buccal, nasal, and topical administration; (b) into a dosage form selected from any of liquid dispersions, gels, aerosols, ointments, creams, tablets, sachets and capsules; (c) into a dosage form selected from any of lyophilized formulations, dry powders, fast melt formulations, controlled release formulations, delayed release formulations, extended release formulations, pulsatile release formulations, and mixed immediate release and controlled release formulations; or (d) any combination thereof.

Solutions or suspensions used for parenteral, intradermal, or subcutaneous application can comprise one or more of the following components: (1) a sterile diluent such as water for injection, saline solution, fixed oils, polyethylene glycols, glycerin, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates; and (6) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition should be sterile and should be fluid to the extent that easy syringability exists. The pharmaceutical composition should be stable under the conditions of manufacture and storage and should be preserved against the contaminating action of microorganisms such as bacteria and fungi. The term "stable", as used herein, means remaining in a state or condition that is suitable for administration to a patient.

The carrier can be a solvent or dispersion medium, including, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent (e.g., an aptamer against sclerostin)

in the required amount in an appropriate solvent with one or a combination of ingredients enumerated above, as required, followed by filtered sterilization. Generally, dispersions are prepared by incorporating at least one aptamer against sclerostin into a sterile vehicle that contains a basic dispersion medium and any other required ingredient. In the case of sterile powders for the preparation of sterile injectable solutions, exemplary methods of preparation include vacuum drying and freeze-drying, both of which will yield a powder of the sclerostin aptamer plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the sclerostin aptamer can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from a pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the aptamer against sclerostin is formulated for topical administration. As used herein "topical administration" refers to the delivery of an aptamer against sclerostin to an animal by contacting, directly or otherwise, a formulation comprising the aptamer against sclerostin to all or a portion of the skin (epidermis) of an animal. The term encompasses several routes of administration including, but not limited to, topical and transdermal. A common requirement for these modes of administration is efficient delivery to the target tissue or stratum. In one aspect, topical administration is used as a means to penetrate the epidermis and dermis and ultimately achieve systemic delivery of the aptamer. In another aspect, topical administration is used as a means to selectively deliver the aptamer against sclerostin to the epidermis or dermis of an animal, or to specific strata thereof.

For topical administration, the aptamer against sclerostin may be formulated into pharmaceutically acceptable ointments, creams, lotions, eye ointments, eye drops, ear drops, impregnated dressings, and aerosols, medicated powders, medicated adhesives, foams, and may contain appropriate conventional additives or excipients, including, for example, preservatives or solvents to assist drug penetration, and emollients in ointments, gels, and creams. Such topical formulations may also contain compatible conventional carriers, for example ethanol or oleyl alcohol for lotions. Such carriers may constitute from about 1% to about 98% by weight of the formulation; more usually, such carriers will constitute up to about 80% by weight of the formulation. Specific formulations for the topical delivery of aptamers are described in the art.

In one embodiment, an aptamer against sclerostin is prepared with a carrier that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions can also be used as pharmaceutically acceptable carriers. These can be prepared according to methods known to those skilled in the art.

Additionally, suspensions of the aptamer against sclerostin may be prepared as appropriate oily injection suspensions. Suitable lipophilic solvents or vehicles include fatty oils, such as sesame oil, or synthetic fatty acid esters, such as ethyl oleate, triglycerides, or liposomes. Nonlipid polycationic amino polymers may also be used for delivery. Optionally, the suspension may also include suitable stabilizers or agents to increase the solubility of the compounds and allow for the preparation of highly concentrated solutions.

In some cases, it may be especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of a aptamer against sclerostin calculated to produce the desired therapeutic effect in association with the required pharmaceutical carrier. The specification for the dosage unit forms of the aptamer against sclerostin described herein are dictated by and directly dependent on the unique characteristics of the particular aptamer against sclerostin and the particular therapeutic effect to be achieved, and the limitations inherent in the art of compounding such an active agent for the treatment of individuals.

Pharmaceutical compositions comprising at least one aptamer against sclerostin can include one or more pharmaceutical excipients. Examples of such excipients include, but are not limited to, binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel PH101 and Avicel PH102, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, crospovidone, sodium starch glycolate, and mixtures thereof; (4) lubricants, including agents that act on the flowability of a powder to be compressed, include magnesium stearate, colloidal silicon dioxide, such as Aerosil 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel PH101 and Avicel PH102; lactose such as lactose monohydrate, lactose anhydrous, and Pharmatose DCL21; dibasic calcium phosphate such as Emcompress; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet (trademark of MAFCO), bubble gum flavor, fruit flavors, and the like; and (10) effervescent agents, including effervescent couples such as an organic acid and a carbonate or bicarbonate.

EXAMPLES

The present invention is further described by the following examples, but the scope of the present invention is not limited to the described examples.

Example 1. Enrichment and Selection of High Affinity Aptamers Against Sclerostin The ssDNA library consists an 18 nt conserved region at each end and a central randomized region. Two ssDNA libraries with different length of randomized sequence were used in this project. The long ssDNA library contains a 40 nt and random region (SEQ ID NO:26)
(5'-CGTACGGTCGACGCTAGC-(N)$_{40}$-CACGTGGAGCTCGGATCC-3')

and the short ssDNA contains a 25 nt random region (SEQ ID NO: 27)
(5'-CGTACGGTCGACGCTAGC-(N)$_{25}$-CACGTGGAGCTCGGATCC-3').

A forward primer (SEQ ID NO: 28)
(FP: 5'-CGTACGGTCGACGCTAGC-3')

and a biotinylated reverse primer (SEQ ID NO: 29)
(Bio-RP: 5'-biotin-GGATCCGAGCTCCACGTG-3')

were synthesized for the amplification of ssDNA during selection. All oligos were purified by HPLC after synthesis.

Protein-SELEX methodology was performed to identify high affinity aptamers (Ellington and Szostak 1990, Tuerk and Gold 1990). 100-30 pmole His$_6$-sclerostin protein was immobilized on NTA magnetic beads at 4° C. for 1 h (Murphy, Fuller et al. 2003). 1 nmole ssDNA library was denatured at 95° C. for 5 min and rapidly cooled down to 4° C. followed by incubation with immobilized sclerostin protein at R.T. for 0.5-1 h. Unbound sequences were removed with washing buffer. After washing, the bound DNAs-protein-NTA were collected, resuspended with H$_2$O/Tween20 and applied to PCR amplification. PCR was performed with unmodified forward primer and 1 Biotinylated reverse primer (step 1:95° C. 1 min for initial denaturation; step 2:95° C. 30 s for denaturation, 56° C. 30 s for annealing, 72° C., 30 s for elongation, repeated for 12 cycles; and step 3:72° C. 5 min for final extension). PCR products were applied to streptavidin magnetic beads through Biotin-streptavidin binding. Single stranded sequences were regenerated by treating with 0.2 M NaOH. Negative selection was performed against other His-tagged non-relevant proteins immobilized on the NTA magnetic beads. 20 rounds of SELEX in total was performed for each selection. The DNA pool from the final round was sent for high-throughput Next Generation Sequence (NGS).

Figure 1B:
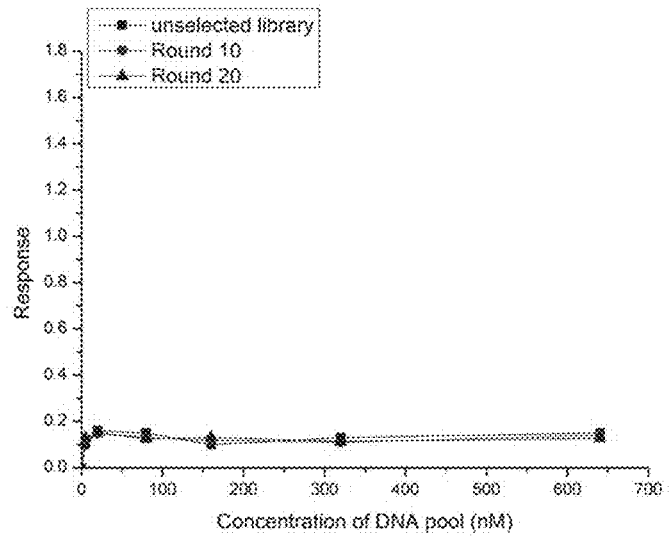

FIG. 1 shows that the affinity of the DNA pool to sclerostin increases after the 10th and 20th rounds of selection, indicating that high-affinity sclerostin aptamers are enriched by SELEX.

Example 2. Specificity Characterization of the Candidate Sclerostin Aptamers

According to the NGS results, representative aptamers with high occurrence were synthesized for specificity assay. Detailed sequences of these aptamer candidates were listed in Table 1.

For determining the specificity of aptamer candidates to sclerostin, representative aptamer candidates and random sequence (RS) (negative control) were synthesized with N-terminal biotinylated modification and 1 µM of each aptamer/RS were used to determine the specificity to sclerostin using an Enzyme-Linked OligoNucleotide Assay (ELONA). 160 ng purified recombinant human sclerostin was coated to 96-well microtiter plate in 100 µl PBS by incubating at 4° C. overnight. The plate was then blocked with blocking buffer (PBS, 0.1% Tween 20 and 1% BSA) for 1 h at room temperature and washed with SELEX B&W buffer (PBS, 1 mM MgCl2, 0.1% Tween 20 and 0.1% BSA) for 4 times. The aptamer candidates were denatured at 95° C. for 10 min and rapidly cooled on ice for 10 min before use. 1 µM biotinylated aptamers were added into each well, then added SELEX B&W buffer to 100 µl and incubated for 45 min at room temperature with continuous gentle shaking. After binding, the plate was washed with SELEX B&W buffer for 4 times to remove non-specific and very weak binding, followed by washing with PBST+0.1% BSA for 4 times. 100 µl streptavidin-HRP/goat anti-human IgG Fc-HRP (1:10000 dilute into PBST+0.1% BSA) was added to each well and incubated for 30/60 min and washed with PBST+0.1% BSA for 4 times. 50 µl TMB was added to each well and incubated for 20 min. The reaction was stopped by adding 50 µl 2 M H2SO4. Absorbance at 450 nm was measured with microplate reader (Stoltenburg, Krafcikova et al. 2016). For determining the binding ability of the aptamer candidates to hepatocytes/PBMCs, the characterization steps were similar with ELONA. 300,000 cells were incubated with each aptamer candidates and the centrifugations were used for washing and separation purposes.

Figure 2A:
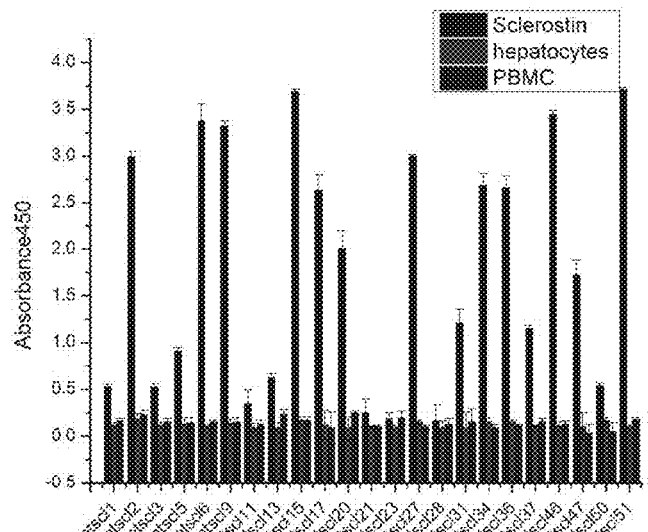
FIG. 2. The specificity characterization of the aptamer candidates. Compared with binding to hepatocytes and PBMC, the aptamer candidates show high selectivity for human sclerostin.
Figure 2B:
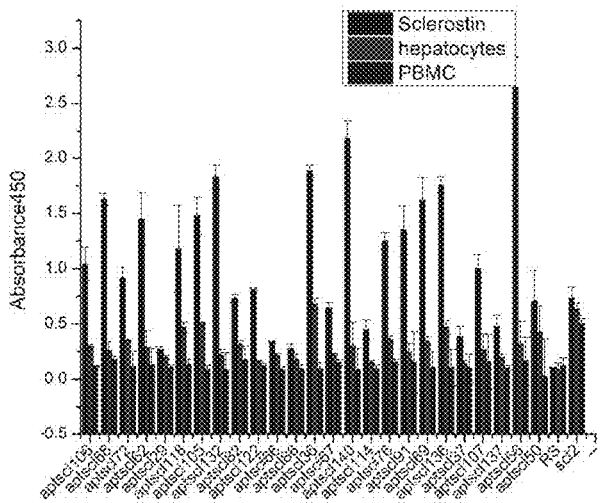
Figure 2C:
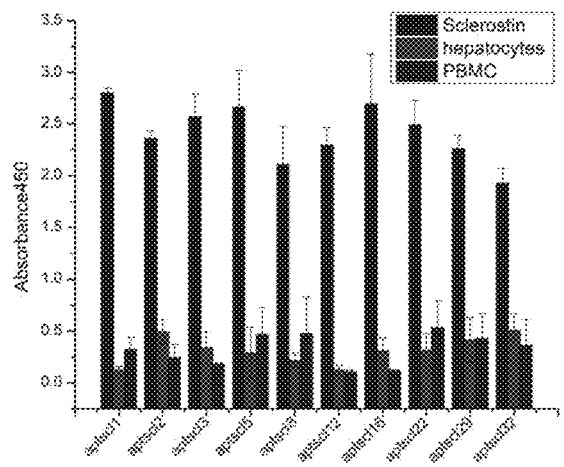

Aptamer candidates identified from both long and short ssDNA libraries showed high selectivity to human sclerostin when comparing the bindings to hepatocytes and PBMCs (FIG. 2). Aptamer candidates aptscl 6, 9, 15, 27, 34, 36, 46, 51, 56, 132 and 140 which identified from the long ssDNA library, aptscl 1, 2, 3, 5, 8, 12. 16, 22, 29 and 32 which identified from the short ssDNA library showed high binding specificity to sclerostin and therefore were chosen for the following affinity characterization.

Example 3. Binding Affinity Characterization of the Candidate Sclerostin Aptamers An Enzyme-linked OligoNucleotide Assay (ELONA) was performed to determine the binding affinity of the aptamer candidates to sclerostin (Drolet, Moon-McDermott et al. 1996). Similarly, an Enzyme-linked ImmunoSorbent Assay (ELISA) was performed to determine the binding affinity of anti-sclerostin antibody to human sclerostin (Engvall and Perlmann 1971). 160 ng purified recombinant human sclerostin was coated to 96-well microtiter plate in 100 µl PBS by incubating at 4° C. overnight. The plate was then blocked with blocking buffer (PBS, 0.1% Tween 20 and 1% BSA) for 1 h at room temperature and washed with SELEX B&W buffer (PBS, 1 mM MgCl2, 0.1% Tween 20 and 0.1% BSA) for 4 times. The aptamer candidates were denatured at 95° C. for 10 min and rapidly cooled on ice for 10 min before use. Appropriate concentrations of biotinylated aptamers/antibody were added into each well, then added SELEX B&W buffer to 100 µl and incubated for 45 min at room temperature with continuous gentle shaking. After binding, the plate was washed with SELEX B&W buffer for 4 times to remove non-specific and very weak binding, followed by washing with PBST+0.1% BSA for 4 times. 100 µl streptavidin-HRP/goat anti-human IgG Fc-HRP (1:10000 dilute into PBST+0.1% BSA) was added to each well and incubated for 30/60 min and washed with PBST+0.1% BSA for 4 times. 50 µl TMB was added to each well and incubated for 20 min. The reaction was stopped by adding 50 µl 2 M H2SO4. Absorbance at 450 nm was measured with microplate reader (Stoltenburg, Krafcikova et al. 2016). Data was analyzed with Origin software (OriginLab, Northampton, MA). A non-linear curve fitting model Hyperbl was used to plot the binding curve. Equation of Hyperbl model is $y=P1*x/(P2+x)$ and P2 is the Kd value.

Figure 3:
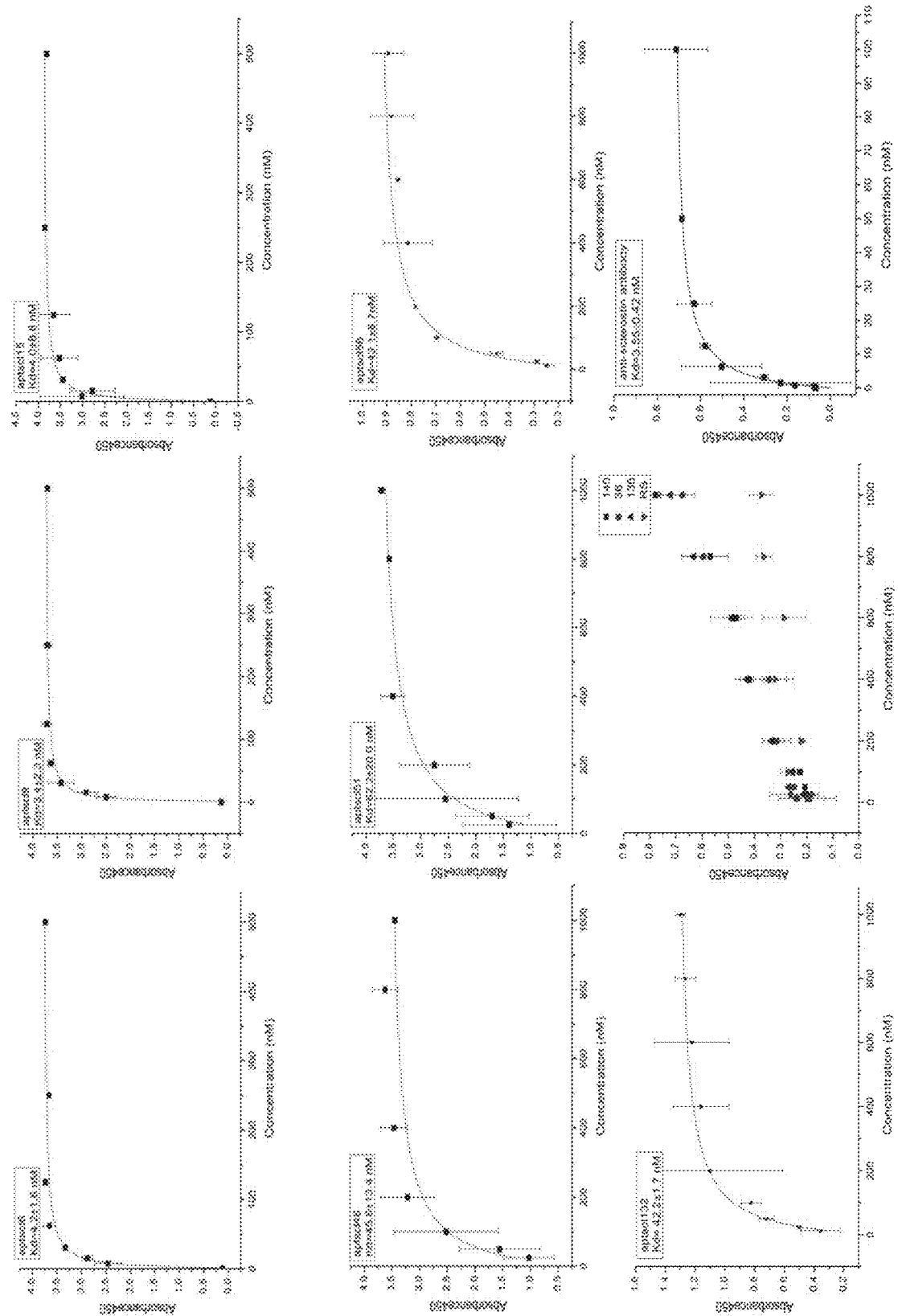
FIG. 3. Binding affinity of the aptamer candidates identified from ssDNA library with a 40 nt random region to recombinant human sclerostin. The dissociation constant values (Kd) for aptamer candidates and antibody to sclerostin was calculated by non-linear curve fitting analysis. The Kd value for each aptamer candidate to sclerostin was: 4.2 nM for aptscl 6, 3.4 nM for aptscl 9, 45.6 nM for aptscl 15, 43.1 for aptscl 46, 43.1 nM for aptscl 56 and 42.2 nM for aptscl 132, respectively. The Kd value was 3.55 nM for anti-sclerostin antibody to sclerostin.
Figure 4:
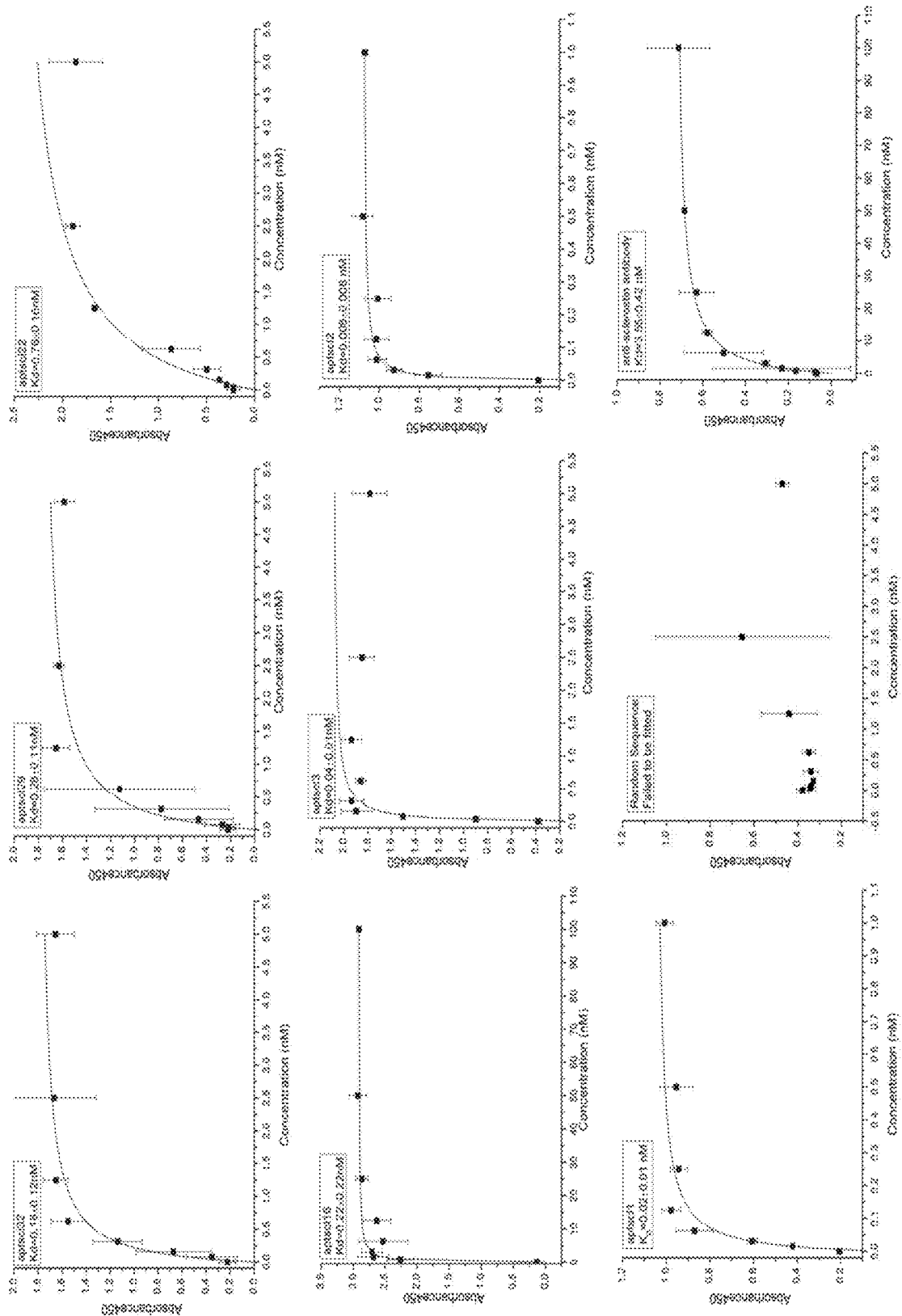
FIG. 4. Binding affinity of the aptamer candidates identified from ssDNA library with a 25 nt random region to recombinant human sclerostin. The dissociation constant value (Kd) for each candidate was calculated by non-linear curve fitting analysis. The Kd value for each aptamer candidate and antibody was: 0.18 nM for aptscl 32, 0.28 nM for aptscl 29, 0.76 nM for aptscl 22, 0.22 for aptscl 16, 0.04 nM for aptscl 3, 0.006 nM for aptscl 2 and 0.02 nM for aptscl 1, respectively. The Kd value was 3.55 nM for anti-sclerostin antibody to sclerostin.
Figure 4:
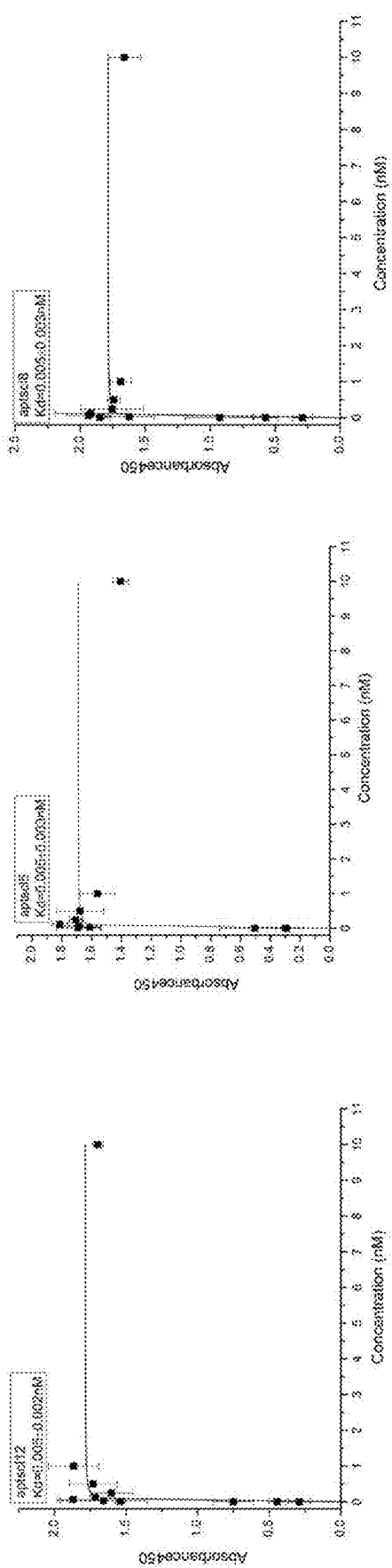
Figure 5A:
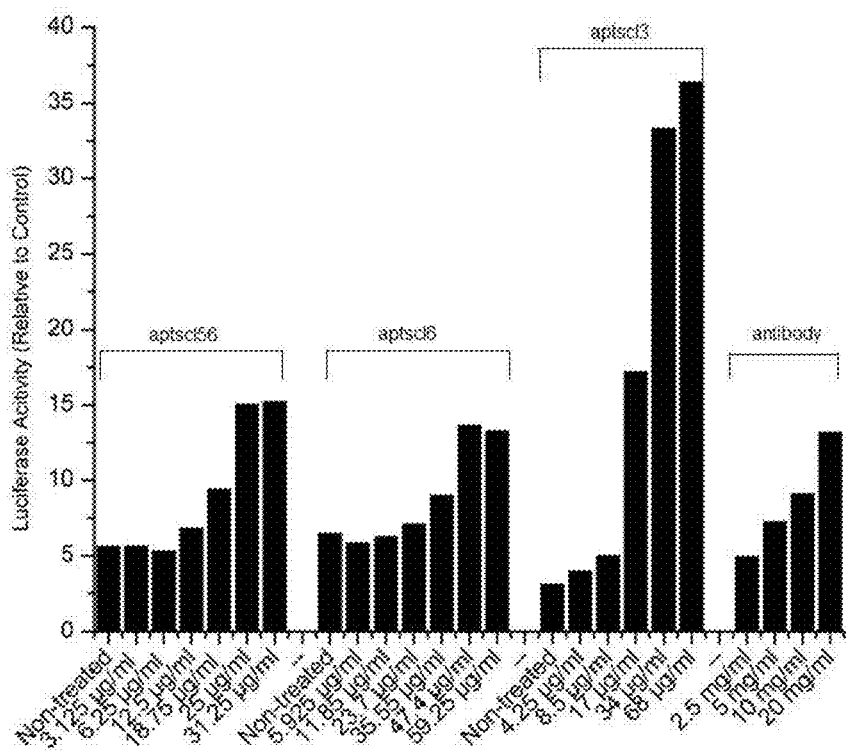
FIG. 5. Inhibition potency assessment of the aptamer candidates and antibody using TOP-Wnt-induced luciferase reporter assay. (A) The luciferase activity of Wnt signaling in MC3T3-E1 cells treated with aptamer candidates in comparison with antibody. Aptscl 56, aptscl 6, aptscl 3 and anti-sclerostin antibody can effectively inhibit sclerostin's antagonistic effect on Wnt signaling and release the Wnt-induced luciferase activity. The response was stable when the concentrations of aptscl 56 and 6 reached to 25 and 47.4 μg/ml, respectively. When treated with antibody, the response was still not stable with the concentration increasing to 20 mg/ml in this experiment. (B) The inhibition potency analysis of aptscl 56. The EC50 for aptscl 56 was 19.7 μg/ml. (C) The inhibition potency analysis of aptscl 6. The EC50 for aptscl 6 was 36.8 μg/ml. (D) The inhibition potency analysis of aptscl 3. The EC50 for aptscl 3 was 18.2 μg/ml.
Figure 5B:
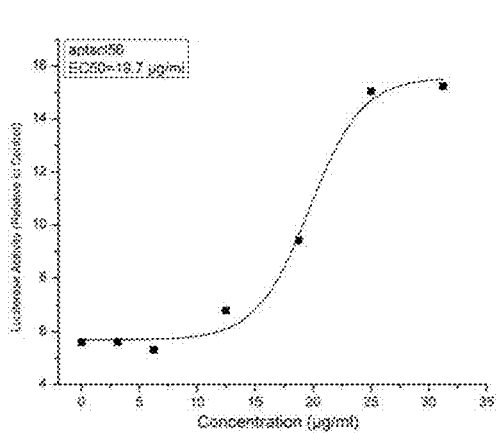
Figure 5C:
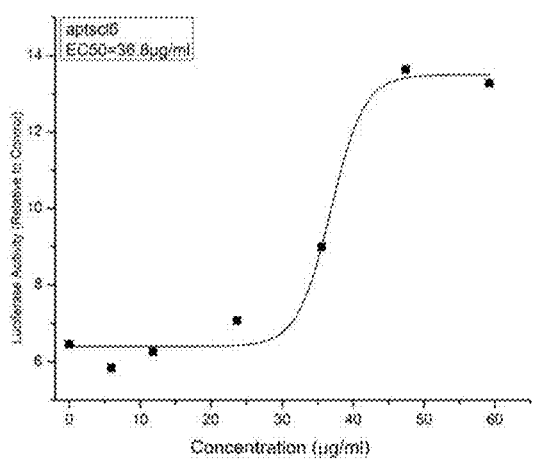
Figure 5D:
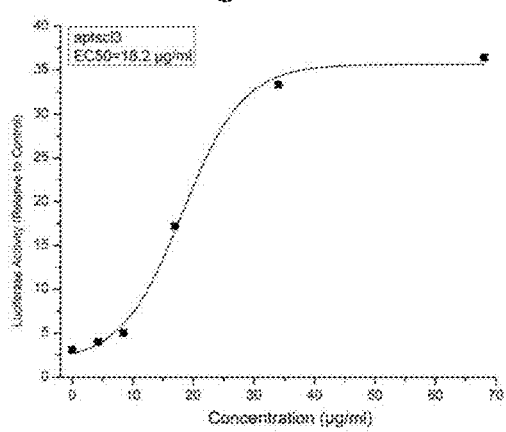

For the aptamer candidates which were identified from ssDNA library containing a 40 nt random region, aptscl 6, 9, 15, 46, 56 and 132 showed high affinity to sclerostin with dissociation constant (Kd) value at nanomolar level (Kd value was 4.2, 3.4, 45.6, 43.1 and 42.2 nM, respectively) (FIG. 3). While aptscl 36, 140, 136 and the random sequence (RS) were failed to be fitted. For the aptamer candidates which were identified from ssDNA library containing a 25 nt random region, aptscl 32, 29, 22, 16, 3, 2 and 1 showed higher binding affinity to sclerostin with Kd value at 0.18, 0.28, 0.76, 0.02, 0.04, 0.006 and 0.02 nM, respectively (FIG. 4). The random sequence showed low binding ability to sclerostin and failed to be fitted. In comparison, the Kd value of anti-sclerostin antibody to sclerostin was 3.55 nM.

Example 4. In Vitro Evaluation of the Inhibitory Ability of the Candidate Sclerostin Aptamer on the Activity of Osteosclerosis To study the inhibition potency of aptamers against sclerostin's antagonistic effect on Wnt signaling, a TOP-Wnt induced luciferase reporter assay was used in osteoblast MC3T3-E1 cells (van Bezooijen, Svensson et al. 2007, Shum, Chan et al. 2011).

MC3T3-E1 cells were seeded in 24-well plates and cells were transfected with corresponding reporter plasmid (100 ng), Wnt3a plasmid (800 ng) and sclerostin plasmid (800 ng) as necessary using FuGENE HD transfection reagent (Promega) in the following day. 10 hours after transfection, culture medium was changed to fresh medium and cells were treated with aptamers/antibody. 24 hours after treatment, each well of cells was lysed with 100 µl passive lysis buffer and 20 µl was taken for analysis. The Luciferase Assay Reagent II and Stop & Glo Reagent were prepared and added automatically by SpectraMax i3x Multi-Mode Detection Platform (Molecular Device) according to the manufacturer's protocol (Promega) and data was analyzed accordingly (Grentzmann, Ingram et al. 1998, McNabb, Reed et al. 2005).

As shown in FIG. 5, aptscl 56, aptscl 6, aptscl 3 and anti-sclerostin antibody can effectively inhibit sclerostin's antagonistic effect on Wnt signaling and release the Wnt-induced luciferase activity. The inhibition to sclerostin was dose dependent and the response was stable when the concentrations of aptscl 56 and 6 reached to 25 and 47.4 µg/ml, respectively. While treated with antibody, the response was still not stable with the concentration increasing to 20 mg/ml. Furthermore, the inhibition potency of aptscl 56, aptscl 6 and aptscl 3 was analyzed with non-linear curve fitting. The EC50 for aptscl56, aptscl6 and aptscl 3 was 19.7 µg/ml, 36.8 µg/ml and 18.2 µg/ml, respectively.

TABLE 1

Sequences of osteosclerosin aptamer candidates

| Name | SEQ ID NO | Sequence against sclerostin (5' to 3') | Length (nt) | Initial library | $K_d$ (nM) | $EC_{50}$ (µg/ml) |
|---|---|---|---|---|---|---|
| aptscl 56 | 1 | CGGGGTGTGGGTTCGTCGTTAGCTTGATTT GGCAGCTGCC | 40 | Long | 43.1 | 19.7 |
| aptscl 132 | 2 | CCCAGACGAGACACCTCATGCTTTTCCCC GGGGGAGGGGTAT | 42 | Long | 42.2 | No Inhibition |
| aptscl 6 | 3 | CGTACGGTCGACGCTAGCTGGAAGGGTGG GGGCGGGGGGTCCTCGCCTCGAACGTACG CACGTGGAGCTCGGATCC | 76 | Long | 4.2 | 36.8 |
| aptscl 9 | 4 | CGTACGGTCGACGCTAGCTGGGGGTAGGG GGACCCTGGCTAGTTAGTCACCGTTTCGA CACGTGGAGCTCGGATCC | 76 | Long | 3.4 | No Inhibition |
| aptscl 15 | 5 | CGTACGGTCGACGCTAGCGAGGGGGCCA ACTATGCTTAGTGGGGGGGTTGACCGTAT CCACGTGGAGCTCGGATCC | 76 | Long | 4 | No Inhibition |

TABLE 1-continued

Sequences of osteosclerosin aptamer candidates

| Name | SEQ ID NO | Sequence against sclerostin (5' to 3') | Length (nt) | Initial library | $K_d$ (nM) | $EC_{50}$ (μg/ml) |
|---|---|---|---|---|---|---|
| aptscl 46 | 6 | CGTACGGTCGACGCTAGCGGGTGGATTAA GGGGGCCCCGTCTGTAGGCGATTGGCGAA CACGTGGAGCTCGGATCC | 76 | Long | 45.6 | No Inhibition |
| aptscl 51 | 7 | CGTACGGTCGACGCTAGCTGGGGGTAGGG GGTCCTTGGCTACGGTGATTCGGATGTGA CACGTGGAGCTCGGATCC | 76 | Long | 62.2 | No Inhibition |
| aptscl 1 | 8 | CGTACGGTCGACGCTAGCTCTTGTTCATC GATCCTACGCACGTGGAGCTCGGATCC | 56 | Short | 0.02 | No Inhibition |
| aptscl 2 | 9 | CGTACGGTCGACGCTAGCCAGCCAAAGAC AGAGATGCACGTGGAGCTCGGATCC | 54 | Short | 0.006 | No Inhibition |
| aptscl 3 | 10 | CGTACGGTCGACGCTAGCTGTTGTACATC GCCTTACGCACGTGGAGCTCGGATCC | 55 | Short | 0.04 | 18.2 |
| aptscl 5 | 11 | CGTACGGTCGACGCTAGCTGTTGTTCATC GACTTGACGCACGTGGAGCTCGGATCC | 56 | Short | 0.005 | No Inhibition |
| aptscl 8 | 12 | CGTACGGTCGACGCTAGCCGGCGAAATTG CTACCACGTGGAGCTCGGATCC | 51 | Short | 0.005 | No Inhibition |
| aptscl 12 | 13 | CGTACGGTCGACGCTAGCCGTTGACTCGT TGCTACACGTGGAGCTCGGATCC | 52 | Short | 0.005 | No Inhibition |
| aptscl 16 | 14 | CGTACGGTCGACGCTAGCTGGTTTCATCG ATCGTATCCACGTGGAGCTCGGATCC | 55 | Short | 0.61 | No Inhibition |
| aptscl 22 | 15 | CGTACGGTCGACGCTAGCTGGGTTTATCG ACTAGTTCCACGTGGAGCTCGGATCC | 55 | Short | 0.76 | No Inhibition |
| aptscl 29 | 16 | CGTACGGTCGACGCTAGCCGGAGACCTGA GGTTCACGTGGAGCTCGGATCC | 51 | Short | 0.28 | No Inhibition |
| aptscl 32 | 17 | CGTACGGTCGACGCTAGCTGTGTTAATCG CCGTACCTCCACGTGGAGCTCGGATCC | 56 | Short | 0.18 | No Inhibition |
| Antibody | — | — | 145.9 kDa | | 3.55 | 100 |

Example 5. Truncation and Characterization of Aptscl3

Figure 6A:
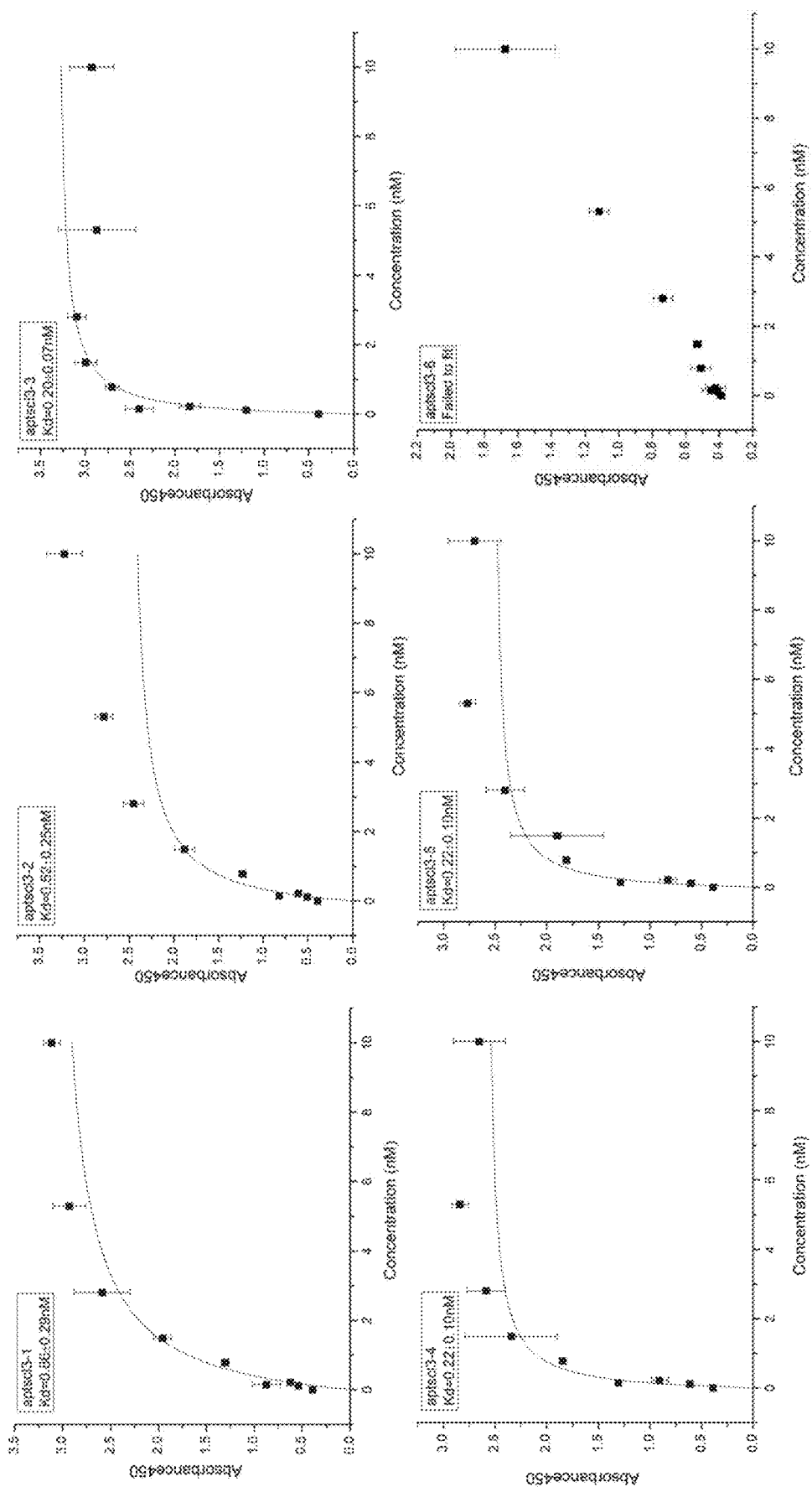
FIG. 6. Characterization of aptscl 3 truncations to sclerostin. (A) Truncations aptscl 3-1, -2, -3, -4 and -5 remained high affinity to sclerostin, while aptscl 3-6 showed low binding ability to sclerostin and failed to fit for the affinity analysis; (B) Truncation aptscl 3-5 which remained high binding affinity reserved high inhibition potency to sclerostin's antagonistic effect on Wnt signaling pathway in cells (EC50=28.4 μg/ml).
Figure 6B:
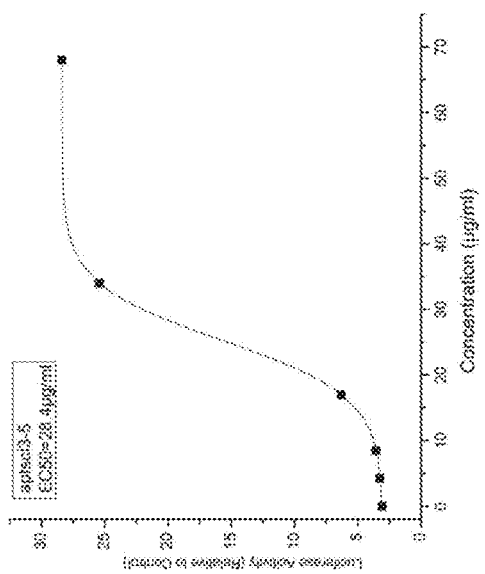

Aptscl3 which showed high affinity and inhibition potency to sclerostin was truncated (Table 2). Binding affinity and in vitro inhibition potency were performed using the same protocols in previous studies. Aptscl 3-1, -2, -3, -4 and -5 remained high binding affinity to sclerostin, with the Kd value at 0.86, 0.52, 0.2 and 0.22 nM, respectively. While aptscl 3-6 failed to fit the binding curve at this concentration range, indicating a low binding ability to sclerostin (FIG. 6a). Furthermore, aptscl3-5 reserved high inhibition potency to sclerostin's antagonistic effect on Wnt signaling (EC50-28.4 μg/ml) (FIG. 6b).

TABLE 2

Sequence truncation of aptamer candidate aptscl3

| Name | SEQ ID NO | Sequence | Nucleotide | Length (nt) | Affinity (nM) |
|---|---|---|---|---|---|
| aptsc 13 | 10 | CGTACGGTCGACGCTAGCTGTTGTACATCGC CTTACGCACGTGGAGCTCGGATCC | 1-55 | 55 | 0.02 |
| aptsc 13-1 | 19 | GTCGACGCTAGCTGTTGTACATCGCCTTACG CACGTGGAGCTCGGATCC | 7-55 | 49 | 0.86 |
| aptsc 13-2 | 20 | CGTACGGTCGACGCTAGCTGTTGTACATCGC CTTACGCACGTGGAGCTC | 1-49 | 49 | 0.52 |
| aptsc 13-3 | 21 | GCTAGCTGTTGTACATCGCCTTACGCACGTG GAGCTC | 13-49 | 37 | 0.2 |

TABLE 2-continued

Sequence truncation of aptamer candidate aptscl3

| Name | SEQ ID NO | Sequence | Nucleotide | Length (nt) | Affinity (nM) |
|---|---|---|---|---|---|
| aptsc 13-4 | 22 | GTCGACGCTAGCTGTTGTACATCGCCTTACG CACGTG | 7-43 | 37 | 0.22 |
| aptsc 13-5 | 23 | GCTAGCTGTTGTACATCGCCTTACGCACGTG | 13-43 | 31 | 0.22 |
| aptsc 13-6 | 24 | TGTTGTACATCGCCTTACGCACGTG | 19-43 | 25 | |

Example 6. Serum Stability Assessment of Chemically Modified Aptamer Candidates The inventors had selected DNA aptamers against sclerostin and finally developed two truncated aptamers, termed aptscl 56 and aptscl 3-5, which specifically and tightly bound to sclerostin with a dissociation constant in the low nanomolar range. The bulky 2'-O-methyl (2'-OMe) modifications of nucleic acid aptamer have been previously used as a post-selection modification due to their enhanced nuclease resistance and elevated duplex melting temperature as seen in the clinical examples (Fine, Martin et al. 2005; Gupta, Hirota et al. 2014). The 3'-end capping with inverted dT has also been a common strategy among aptamers for diseases therapy in on-going or completed clinical trials (Padilla, Sousa et al. 1999; Ruckman, Green et al. 1998). Taken together, this example is to evaluate whether the serum stability of aptscl 56 and aptscl 3-5 could be improved by 2'-OMe and 3'-terminal Inverted dT (3'-idT) modifications.

Experimental Design

The modified nucleotide was introduced during synthesis. The serum metabolic stability of the modified and unmodified aptamers was evaluated in freshly prepared mouse serum. All the aptamer samples were incubated with 10% and 100% mouse serum at 37° C. for 0, 2, 4, 8, 12, 24, 36, 48 and 72 hours, respectively. At the assigned time, the aptamer samples were flash-frozen in a dry ice bath and then stored at −80° C. until all the samples were harvested for evaluation. The stability of all the aptamer samples was expressed as the band density of intact aptamer remaining after the incubation, which could be determined by agarose gel electrophoresis.

DNA Synthesis Protocol

Modified and unmodified DNA sequences were synthesized on a 1 µmole scale on a K&A H8 standard DNA/RNA Synthesizer using commercially available 5'-O-DMT-2'-deoxynucleoside (ABz, CAc, GiBu and T) phosphoramidite monomers, 5'-O-DMT-2'-O-methyl nucleoside (ABz, CAc, GiBu and T) phosphoramidite monomers and/or 5'-O-DMT-2'-F-nucleoside (ABz, CAc, GiBu and T) phosphoramidite monomers (Beaucage and Caruthers 2001). The modified sequence of aptscl56 was CGGGG TGTGG GTTCG TCGTT AGCTT GATTT GGCAG CTGCCC-idT and the nucleotide underlined was 2'-OMe modified. The modified sequence of aptscl 3-5 was GCTAG CTGTT GTACA TCGCC TTACG CACGT G-idT and the nucleotide underlined was 2'-OMe modified.

Evaluation Protocols:

The band density of all the aptamer samples was assayed by a molecular imager (Bio-Rad) (Klussmann, Nolte et al. 1996, Siller-Matula, Merhi et al. 2012). The binding affinity and in vitro inhibition potency were performed using the same protocols in previous studies.

Results

Figure 7:
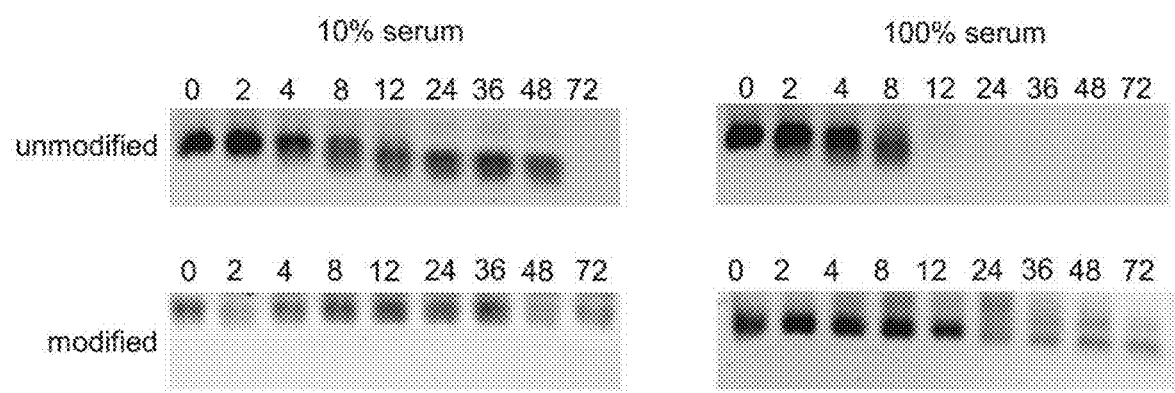
FIG. 7. The serum stability assessment of modified aptscl 56 compared to unmodified aptscl 56. All aptamers were treated with 10% and 100% mouse serum from 0 to 72 hours. Nearly all unmodified aptscl 56 was degraded 48 h after incubation in 10% mouse serum. The 2'-OMe and 3' idT modified aptscl 56 could last 48 h in 10% mouse serum. In 100% serum, the unmodified aptscl 56 was rapidly and fully degraded after 8 h. At 72 h, a small amount of modified aptamer was still remained.

For aptscl 56, the unmodified aptamer was fully degraded after 48 h in 10% serum and remained only for 8 h in 100% serum. The 2'-OMe and 3' idT modified aptscl 56 was remained for 72 h in 10% mouse serum and was degraded after 12 h. At 72 h, a small amount of modified aptamer was still remained (FIG. 7).

Figure 8:
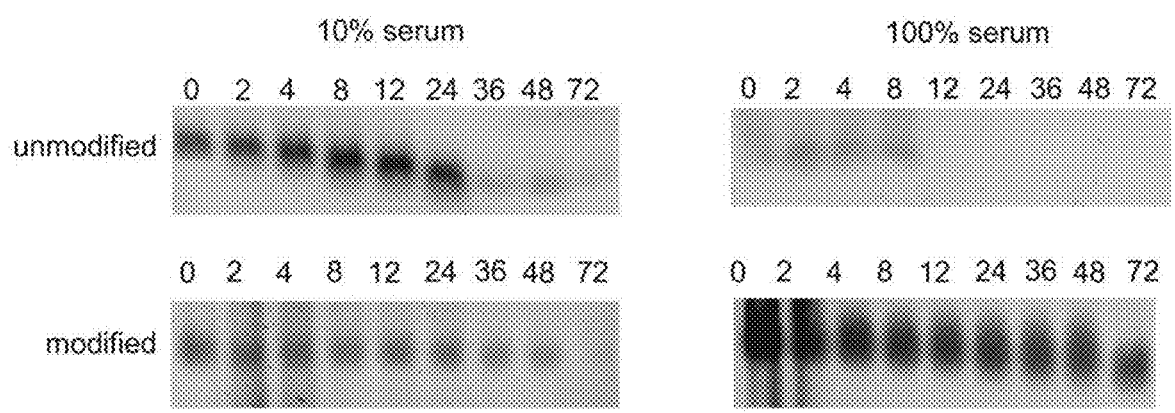
FIG. 8. The serum stability assessment of modified aptscl 3-5 compared to unmodified aptscl 3-5. All aptamers were treated with 10% and 100% mouse serum from 0 to 72 hours. Aptscl 3-5 was degraded after 24 h incubation in 10% mouse serum. The 2'-OMe and 3' idT modified aptscl 3-5 could last 48 h in 10% mouse serum. In 100% serum, the unmodified aptscl 3-5 was rapidly and fully degraded after 8 h, while the modified aptscl 3-5 could remain the integrity after 72 h.

For aptscl 3-5, the unmodified aptamer was degraded 24 h after incubation in 10% mouse serum. The 2'-OMe and 3' idT modified aptscl 3-5 could last 48 h in 10% mouse serum. In 100% serum, the unmodified aptscl 3-5 was rapidly and fully degraded after 8 h, while the modified aptscl 3-5 could remain the integrity after 72 h (FIG. 8).

Figure 9:
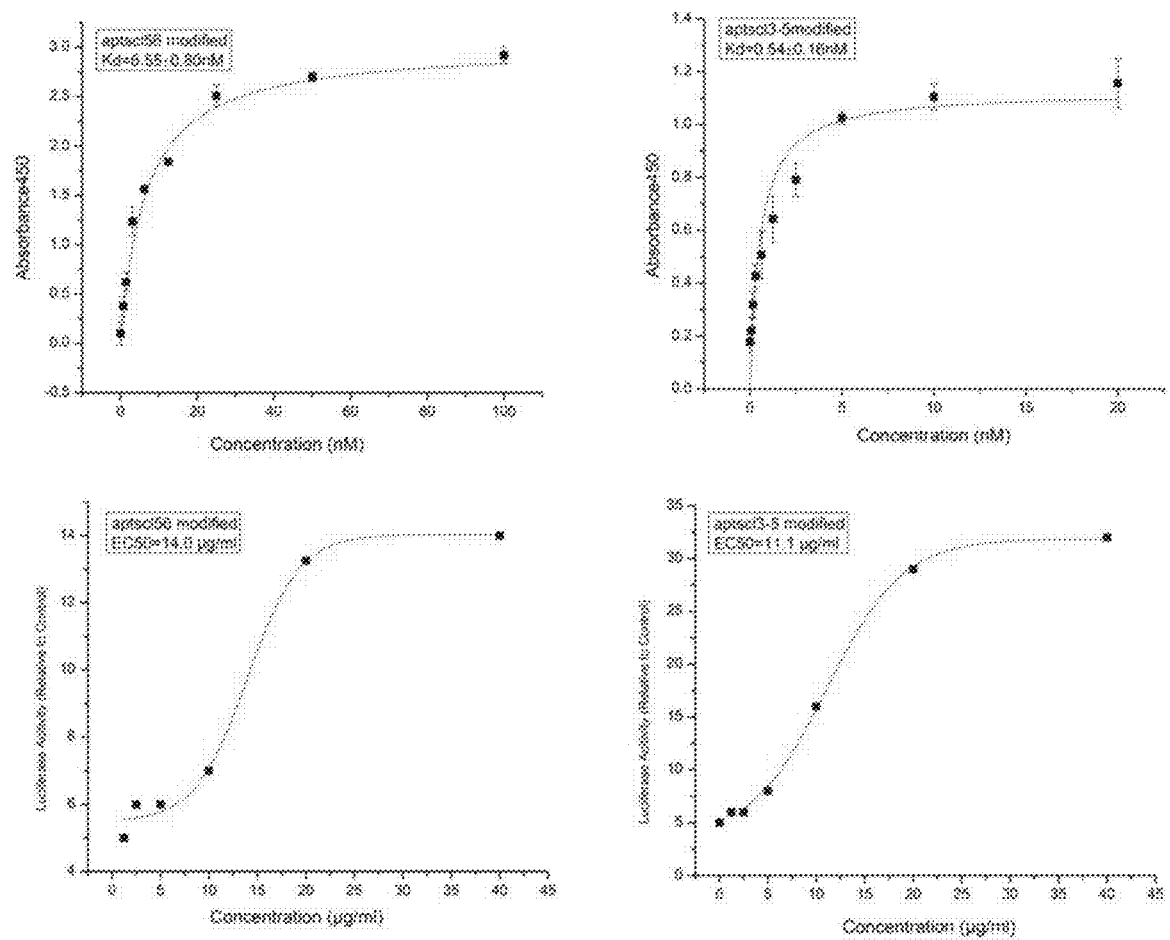
FIG. 9. Affinity and inhibition potency of chemically modified aptscl 56 and aptscl 3-5. With chemical modifications, both aptscl 56 and aptscl 3-5 remained the high affinity and in vitro inhibition potency to sclerostin.

Chemically modified aptscl 56 and aptscl 3-5 showed high binding affinity to sclerostin, with Kd value as 6.55 and 0.54 nM, respectively. Furthermore, chemically modified aptscl 56 and aptscl 3-5 could efficiently inhibit sclerostin's antagonistic effect on Wnt signaling in cells, with the inhibition potency as 14 and 11 µg/ml, respectively (FIG. 9).

Conclusion

The modification with 2'-OMe and 3' idT could further facilitate developing aptscl 56 and aptscl 3-5 toward therapeutic nuclease-resistant aptamers.

Example 7. Aptamers with PEG Modification

This is to determine the plasma pharmacokinetics of the aptamer with and without PEG modification against sclerostin (PEG40K-aptscl 56 and aptscl 56) after subcutaneous administration in rats. The sequence of aptscl 56 is CGGGG TGTGG GTTCG TCGTT AGCTT GATTT GGCAG CTGCCC-idT, and each nucleotide of the start CGGG and the end GCCC is modified with 2'-OMe. On this basis, PEG40K (PEG with a molecular weight of 40,000) is further attached at the 5'-end to obtain PEG40K-aptscl 56.

Experimental Design

The pharmacokinetic studies of the aptamer aptscl56 and PEG40K-aptscl 56 were performed in six-month-old female virgin Sprague-Dawley rats, which were fed ad libitum with a standard laboratory diet and housed under controlled conditions (12 h light cycle, 20° C.). The rats were treated with 6.1 mg/kg aptscl 56 and 25 mg/kg PEG40K-aptscl 56 by a single subcutaneous injection, respectively. Aptscl56 and PEG40K-aptscl 56 were dissolved in saline at the concentration of 1.6 mg/ml and 6.2 mg/ml for administration, respectively (Judith M. Healy, Ryan M. Boomer et al. 2004). Blood samples were collected at different time points (aptscl56: 5 min, 15 min, 30 min, 1 h, 2 h, 4 h, 8 h, 12 h, 24 h; PEG40K-aptscl 56: 30 min, 1 h, 2 h, 4 h, 8 h, 12 h, 24 h, 30 h, 36 h, 48 h, 54 h, 62 h, 70 h, 76 h, 84 h, 96 h, 107 h) from replicate rats (n=6) in each group and plasma was isolated. After treated by proteinase K, the remaining aptscl 56 and PEG40K-aptscl 56 in the plasma were quantified by HPLC.

Evaluation Protocols

Sample preparation: Approximately 800 μl of blood was taken via orbital vein from each rat, and collected into tubes containing sodium-heparin as an anticoagulant (1.8 ml vacu-tainers, BD Biosciences), then put on wet ice immediately (Healy, Lewis et al. 2004, Perschbacher, Smestad et al. 2015). Plasma was isolated by centrifugation at 6000 g for 10 min at 4° C. as soon as possible within 1 hour after collection and stored at −80° C. until analysis (Healy, Lewis et al. 2004, Siller-Matula, Merhi et al. 2012, Gao, Shen et al. 2016). Prior to analysis, 25 μl digestion buffer (60 mM Tris-HCl, pH 8.0, 100 mM EDTA and 0.5% SDS) and 75 μl of proteinase solution (1 mg/mL proteinase K in 10 mM Tris HCl, pH 7.5, 20 mM $CaCl_2$), 10% glycerol v/v) were added into 50 μl plasma samples. Samples were then incubated at 55° C. overnight with shaking. Following the incubation, samples were centrifuged (14000 rpm; 4° C.; 15 minutes) and 100 μl of the supernatant were taken and transferred to HPLC injection vials (Siller-Matula, Merhi et al. 2012).

HPLC quantification: The HPLC system was equipped with C4 column to quantify PEG40K-aptscl 56 in plasma samples collected at different time points, while C18 column was utilized for quantification of aptscl 56. The method both used a mobile phase elution gradient made from phase A (TEAA [pH 7.0]) and phase B (acetonitrile). Flow rate were both 1.0 mL/min with column oven temperature set at 50° C. The assay injection volume was 20 uL. Standards were prepared in blank rat plasma containing sodium-heparin with different concentrations of aptscl 56 and PEG40K-aptscl 56, respectively (Gao, Shen et al. 2016). All reported concentrations of aptscl56 and PEG40K-aptscl 56 were based on the mass of aptscl 56. Aptamer concentrations in plasma samples were calculated according to the standard curve.

Pharmacokinetic analysis: The Aptscl 56 and PEG40K-aptscl 56 concentrations versus time profile were plotted and analyzed for each rat by software DAS 3.0 (BioGuider Co., Shanghai, China). The resulting pharmacokinetic parameters were averaged. Half-life (t1/2) of the aptamer was calculated according to the time it takes for aptamer to eliminate half of the maximum plasma concentration (Grieken and Bruin 1994). Maximum plasma concentration (Cmax) and the time to maximum plasma concentration (Tmax) were obtained according to pharmacokinetic curves. The area under the curve (AUC) was computed starting at the time the drug was administered and ending when the concentration in plasma was negligible (Rowland, Benet et al. 1973, Toutain and Bousquet-Melou 2004, Siller-Matula, Merhi et al. 2012). Subsequently, the dosing interval in multiple-dose of PEG40K-aptscl 56 was calculated according to the equation: $D=1/1-e^{-Ke \cdot t}$ (Ke: elimination constant, Ke=ln2/T1/2; t: dosing interval; D: dosing ratio-loading dose/maintenance dose) (Birkett 1996, Jambhekar 2012).

Results

Figure 10:
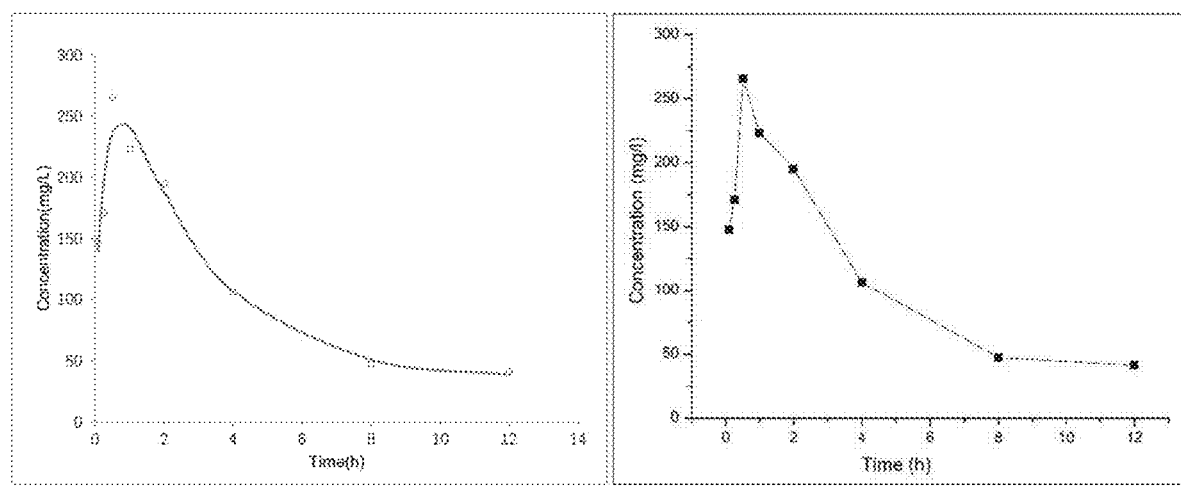
FIG. 10. Pharmacokinetics of a single subcutaneous injection of aptscl 56 in 6 rats: fitted pharmacokinetics curve by software DAS (left, orange), actual pharmacokinetics curve (right).

The lower limit of HPLC quantitation for aptscl 56 was 10 μl/mL with a linear concentration range of 10 μg/mL to 360 μg/mL. The average value of elimination half-life (Elim. T1/2) of aptscl 56 aptamer in Sprague-Dawley rats after subcutaneous administration was 1.8 hours. The average value of Cmax was 265.5 μg/ml with Tmax of 0.5 hours (FIG. 10, Table 3).

Figure 11:
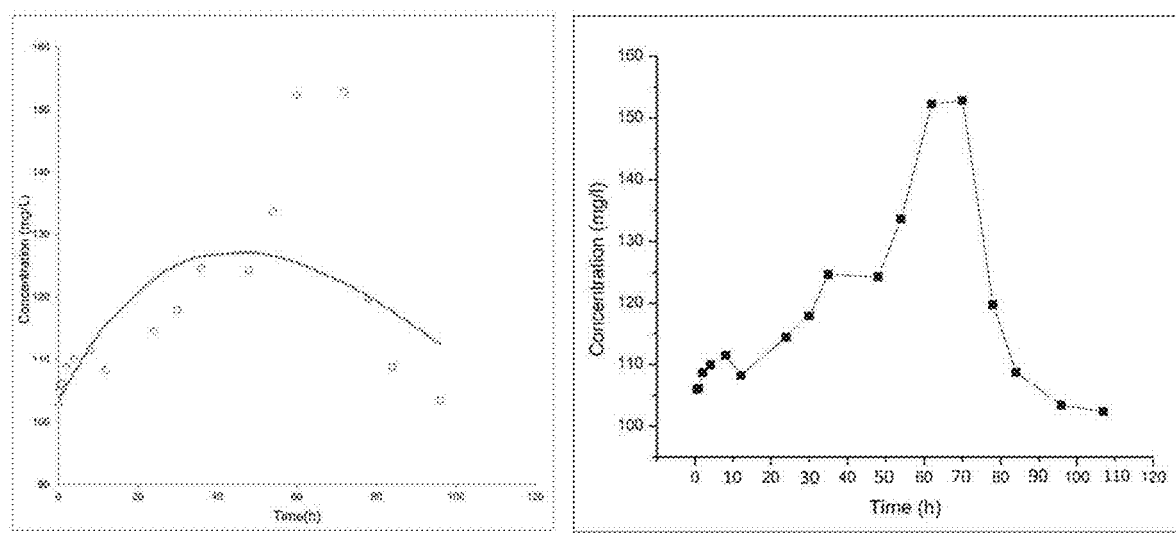
FIG. 11. Pharmacokinetics of a single subcutaneous injection of aptscl 56-PEG in 6 rats: fitted pharmacokinetics curve by software DAS (left), actual pharmacokinetics curve (right).

The lower limit of HPLC quantitation for PEG40K-aptscl 56 was 7.5 μg/mL with a linear concentration range of 7.5 μg/mL to 240 μg/mL. The average value of elimination half-life (Elim. T1/2) of PEG40K-aptscl 56 in Sprague-Dawley rats after subcutaneous administration was 66.9 hours. The average value of Cmax was 152.8 μg/ml with Tmax of 72 hours (FIG. 11, Table 4).

TABLE 3

Pharmacokinetic parameters of aptscl56 administrated s.c.

| Parameter | Units | Mean value |
|---|---|---|
| Tmax | (h) | 0.5 |
| Cmax | (μg/ml) | 265.5 |
| AUC | ((μg h)/ml) | 1205 |
| Elim. T1/2 | (h) | 1.8 |

TABLE 4

Pharmacokinetic parameters of PEG40K-aptscl 56 administrated s.c.

| Parameter | Units | Mean value |
|---|---|---|
| Tmax | (h) | 72 |
| Cmax | (μg/ml) | 152.8 |
| AUC | ((μg h)/ml) | 11802 |
| Elim. $T_{1/2}$ | (h) | 66.9 |

Discussion

Figure 12:
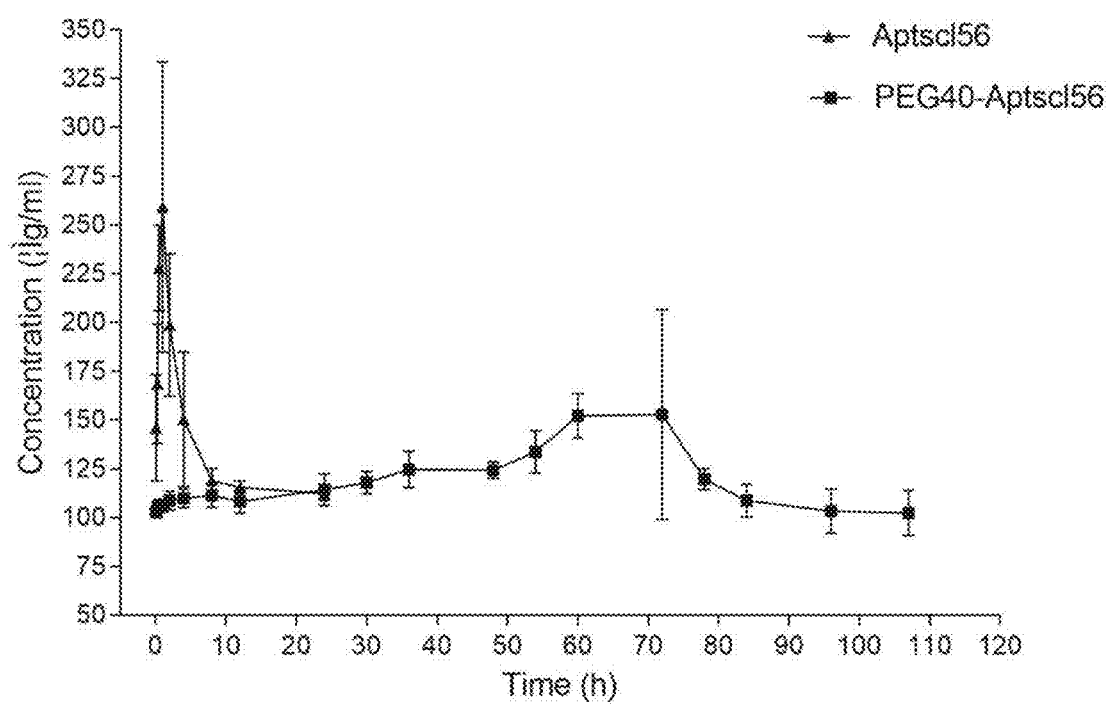
FIG. 12. Pharmacokinetics of a single subcutaneous injection of aptscl 56 (blue) and aptscl 56-PEG (orange) in rats, respectively

This work investigated the pharmacokinetic characteristics of aptscl56-PEG and aptscl 56 subcutaneously administrated in S.D. rats, respectively. Comparing to the 1.8 hours elimination half-life of aptscl 56, the half-life of PEG40K-aptscl 56 was extended dramatically by 65.1 hours. This indicated that PEG had significant effect on prolonging the in vivo residence time of aptscl56. However, the concentrations of PEG40K-aptscl 56 in plasma were integrally lower than the concentration of aptscl56 (FIG. 12). Many studies have demonstrated that size enlargement of PEGylation led to a systematic decrease in absorption into the blood (Caliceti 2003, Kaminskas, Kota et al. 2009). The absorption of aptscl 56 into blood may be hindered by PEGylation.

In pharmacokinetic studies of PEG40K-aptscl 56, it took 60 hours for absorption but 35 hours for elimination. However, the time needed for elimination of most aptamer-PEG is always much longer than absorption (Christopher E. Tucker 1999, Siller-Matula, Merhi et al. 2012). Some studies indicated that size enhancement of PEGylation promoted the accumulation into permeable tissues by the passively enhanced permeation and retention mechanism (Caliceti 2003). Accumulation of PEG40K-aptscl 56 into permeable tissues may be one of the reasons for the quick decline in the elimination phase of pharmacokinetic curve. Further studies on this pharmacokinetic phenomenon of aptscl56-PEG will be conducted for a clear explanation.

Dosing interval in multiple-dose of aptamer could be defined base on its elimination half-life and the dosing ratio of loading dosage and maintenance dosage (Birkett 1996, Jambhekar 2012). The elimination half-life of PEG40K-aptscl 56 is 66.9 hours. If the dosing ratio is 2, the dosing interval equals to elimination half-life (T1/2). If the dosing ratio is less than 2, the dosing interval should be longer than T1/2. In pharmacodynamics study of aptscl56-PEG, the proposed dosing ratio is 1 (loading dosage equals to maintenance dosage). Thus, the dosing interval of PEG40K-aptscl 56 should be a little longer than 66.9 h.

Example 8. Evaluation of the Efficacy of PEGylated Aptamer Candidates on Bone Anabolism in Rats with Osteoporosis Induced by Ovariectomy Treatment protocol of PEG40K conjugated aptamer in osteoporotic rats. In order to evaluate the efficacy of the combination of chemically modified aptscl56/aptscl3 and PEG40K on bone anabolism in ovariectomized-induced osteoporosis rats, 70 female Sprague Dawley rats aged 3 months were subjected to ovariectomy (OVX, n=50) or Sham operation (SHAM, n=20), and no treatment for 2 months. Before treatment, 10 OVX rats and 10 SHAM-operated rats were euthanized as baseline (OVX–BS and SHAM-BS). The remaining SHAM or OVX rats were injected subcutaneously with vehicle (Veh), PEG40K-aptscl 56/aptscl 3 (25 mg/kg) or PEG40K-random sequence (RS, 25 mg/kg) once a week for 6 weeks (n=10 per group). All animals were euthanized 6 weeks after the first injection. Before euthanasia, all animals were injected intraperitoneally with calcein (20 mg/kg) on day 13 and day 3, respectively. After euthanasia, the right femur was collected, and the bone microstructure was examined by micro-CT. The left femur was collected for undecalcified section and further histomorphological analysis. All experiments were performed in accordance with relevant guidelines and regulations, and all experimental procedures were approved by the Animal Ethics Committee and Experimental Safety Committee of Hong Kong Baptist University Micro-CT analysis. Micro-CT (version 6.5, vivaCT40, SCANCO Medical AG, Bassersdorf, Switzerland) was used to analyze the metaphysis of the distal right femur, the metaphysis of the proximal tibia, the fifth lumbar vertebra and the central axis of the right femur. The images of the vertebrae and femur were reconstructed and calibrated with isotropic voxel sizes of 12.5 and 17.5 μm (70 kVp, 114 μA, 200 ms integration time, 260 threshold, 1200 mg HA/cm$^3$), respectively. The same filtering and segmentation values are used for each measurement. The regions of interest (ROI) for cortical and trabecular parameters were defined using Scanco evaluation software. For the right distal femoral metaphysis and the right proximal tibia metaphysis, the entire femur or tibia were reoriented, the middle bone was in parallel to the z axis, and the bone length was measured as the distance between femur containing the proximal and distal transverse plates. Starting from the nearest end of the growth plate, the trabecular regions on 100 consecutive slices at a distance of 1.4 mm from the growth plate were selected. The trabecula was analyzed by manual contouring to exclude cortical bone. For the fifth vertebra, a central area corresponding to 70% of the height of the vertebral body and extending toward the vertebral body from the proximal end to the end of the distal growth plate was selected. The trabecular ROIs were drawn freehand on 100 consecutive sections to ensure that they were in the bone capsule. For the right femoral axis, an automatic threshold algorithm was used to measure 100 slices at the exact center and distal 50% of the femur length. The trabeculaes in contact with the cortical bone were manually removed from the ROI. Bone trabecular parameters were calculated, including trabecular volume per total volume (Tb.BV/TV), trabecular volume mineral density (Tb.vBMD), trabecular thickness (Tb.Th), and number of trabeculae (Tb.N)), trabecular spacing (Tb. Sp), trabecular structure model index (Tb.SMI), trabecular connection density (Tb.conn.D).

Statistical Analysis. Statistical analysis was performed using GraphPad Prism (version 8; GraphPad Software, Inc). All numerical data are expressed as mean±standard deviation. One-way ANOVA and Tukey's post-hoc test were used for all parameters. P<0.05 was considered statistically significant.

Results

For bone trabecular, micro-computed tomography (micro-CT) analysis showed that compared with ovariectomized (OVX) baseline (OVX–BS) rats, the trabecular bone quality of distal femur and proximal tibia, the distal and fifth lumbar vertebrae of SHAM baseline (SHAM-BS) rats is significantly higher, and the trabecular bone structure performance is better (FIG. 13). Six regular injections of PEG40K-aptscl 56/aptscl3, random sequence or vector were used to treat OVX rats at weekly intervals (named OVX+aptscl56, OVX+aptscl3, OVX+RS and OVX+Veh, respectively). SHAM rats were treated with vehicle once a week for 6 weeks (SHAM+Veh) (FIG. 13a). Quantitative analysis of the trabecular regions of the distal femur, proximal tibia and the fifth vertebra showed that the bone mass of OVX+Veh was significantly reduced compared to the SHAM+Veh control (FIG. 13b, c, and d). These data indicate that osteoporosis was successfully induced in OVX rats.

Figure 13A:
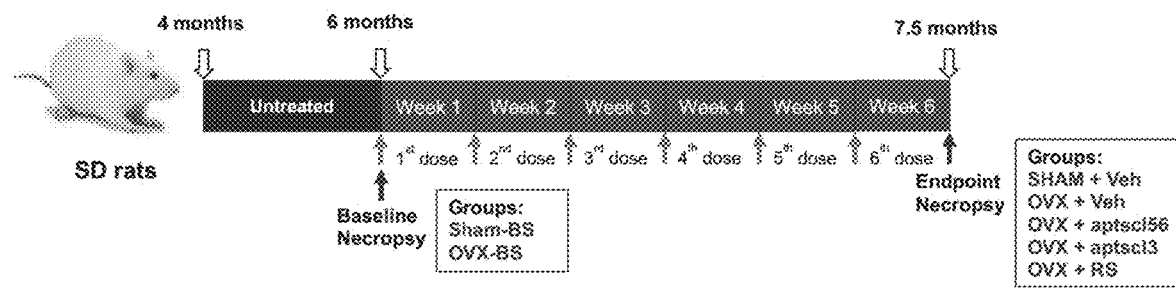
FIG. 13 shows the evaluation of the efficacy of PEG40K-aptscl 56/aptscl 3 on bone metabolism in ovariectomized rats with osteoporosis. (a) A schematic diagram showing the experimental design of the study. (b) Representative 3D microarchitecture images and micro-CT parameters of distal femoral trabeculae of each group. (c) Representative 3D microarchitecture images and micro-CT parameters of proximal tibia trabeculae of each group. (d) Representative 3D microarchitecture images and microCT parameters of the fifth vertebra in each group. Note: BMD: bone mineral density; Tb.BV/TV: trabecular bone relative bone mass; Tb.vBMD: trabecular volume mineral density; Tb.Th: trabecular thickness; Tb.N: trabecular number; Tb.Sp: Trabecular spacing; Tb.conn.D: Trabecular connection density; Tb.SMI: Trabecular structure model index; MAR: Mineral deposition rate; BFR/BS: Bone formation rate; Ob.S/BS: Osteoblast surface; and Ob.N/B.Pm: the number of osteoblasts; PINP: the complete N-terminus of procollagen I; OPG: bone protection. SHAM-BS: SHAM baseline; OVX–BS: OVS baseline before treatment; SHAM+Veh: SHAM rats treated with vehicle; OVX+Veh: OVX rats treated with vehicle; OVX+aptscl56: OVX rats treated with PEG40K-aptscl56; OVX+RS: OVX rats treated with PEG40K-random sequence. Random sequence.
Figure 13B:
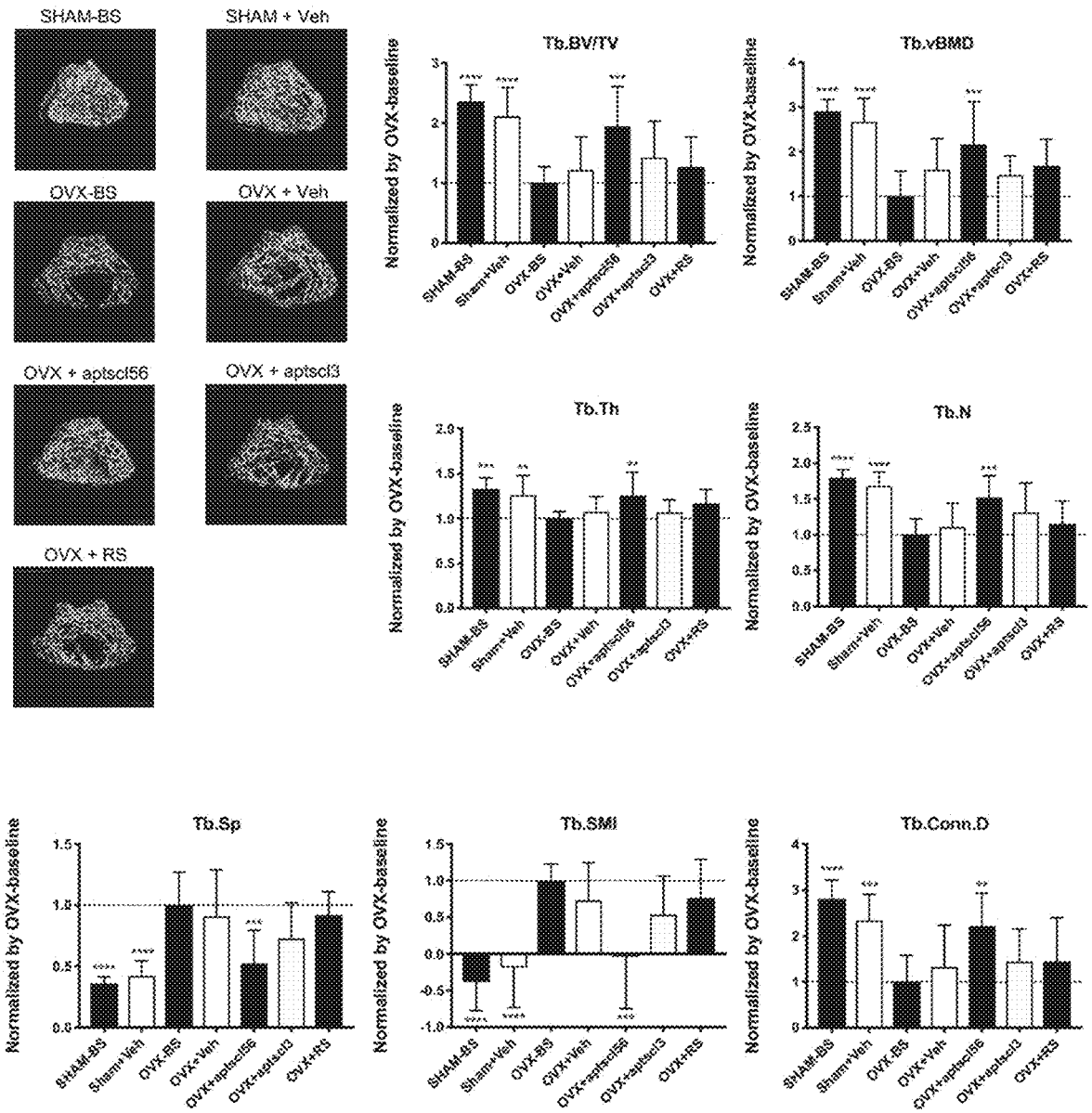
Figure 13C:
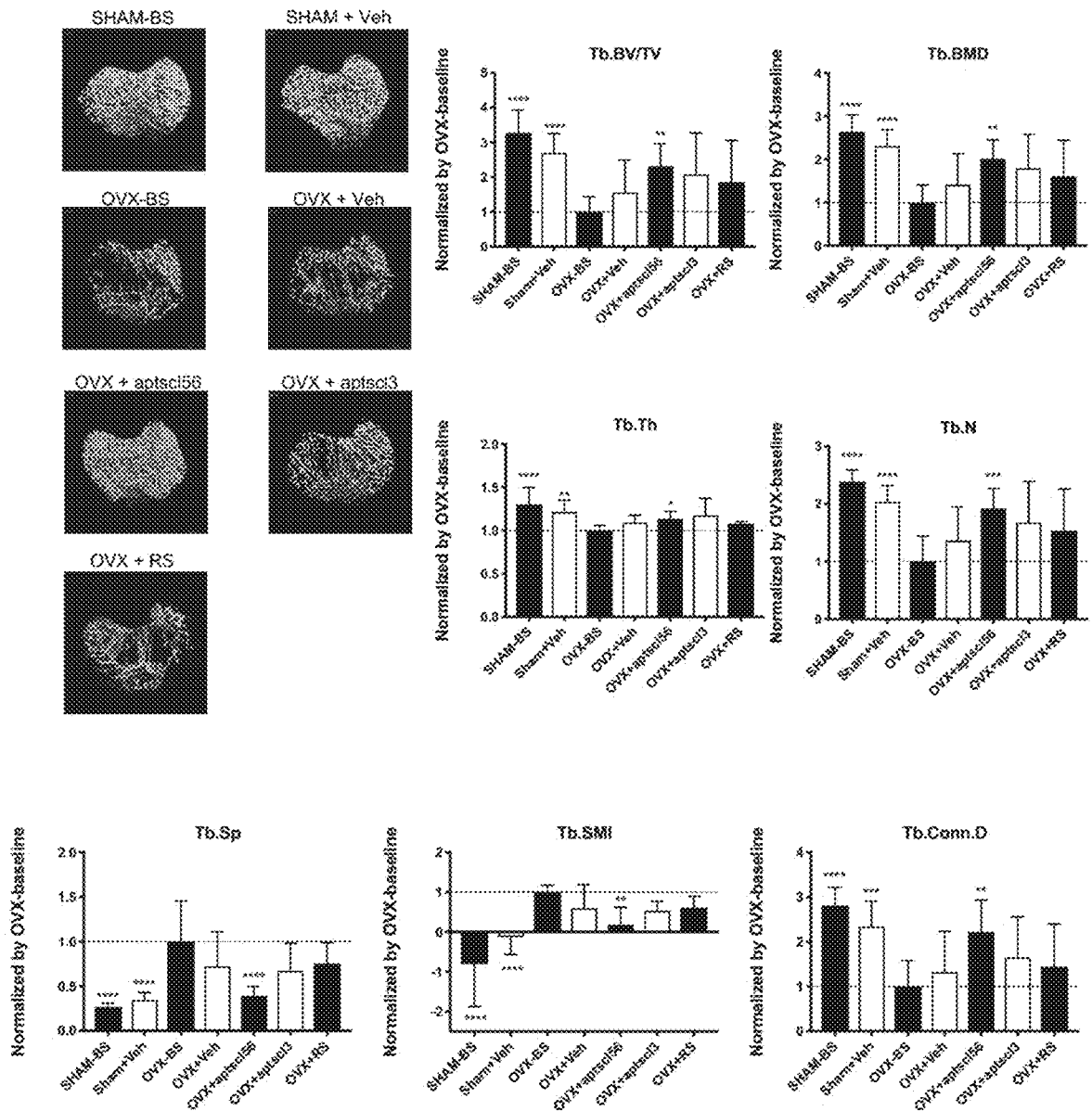

Micro-CT analysis of the metaphyseal region of the distal femur showed that BMD and BV/TV were significantly higher, indicating that compared with OVX–BS, the trabecular bone mass of OVX+aptscl56 rats was significantly increased (P<0.005). Compared with OVX–BS, the trabecular structure of OVX+aptscl56 was also significantly improved (FIG. 13b). However, like the OVX+Veh and OVX+RS groups, the OVX+aptscl 3 group did not show significantly increased bone mass and improved structure compared with OVX–BS.

Figure 13D:
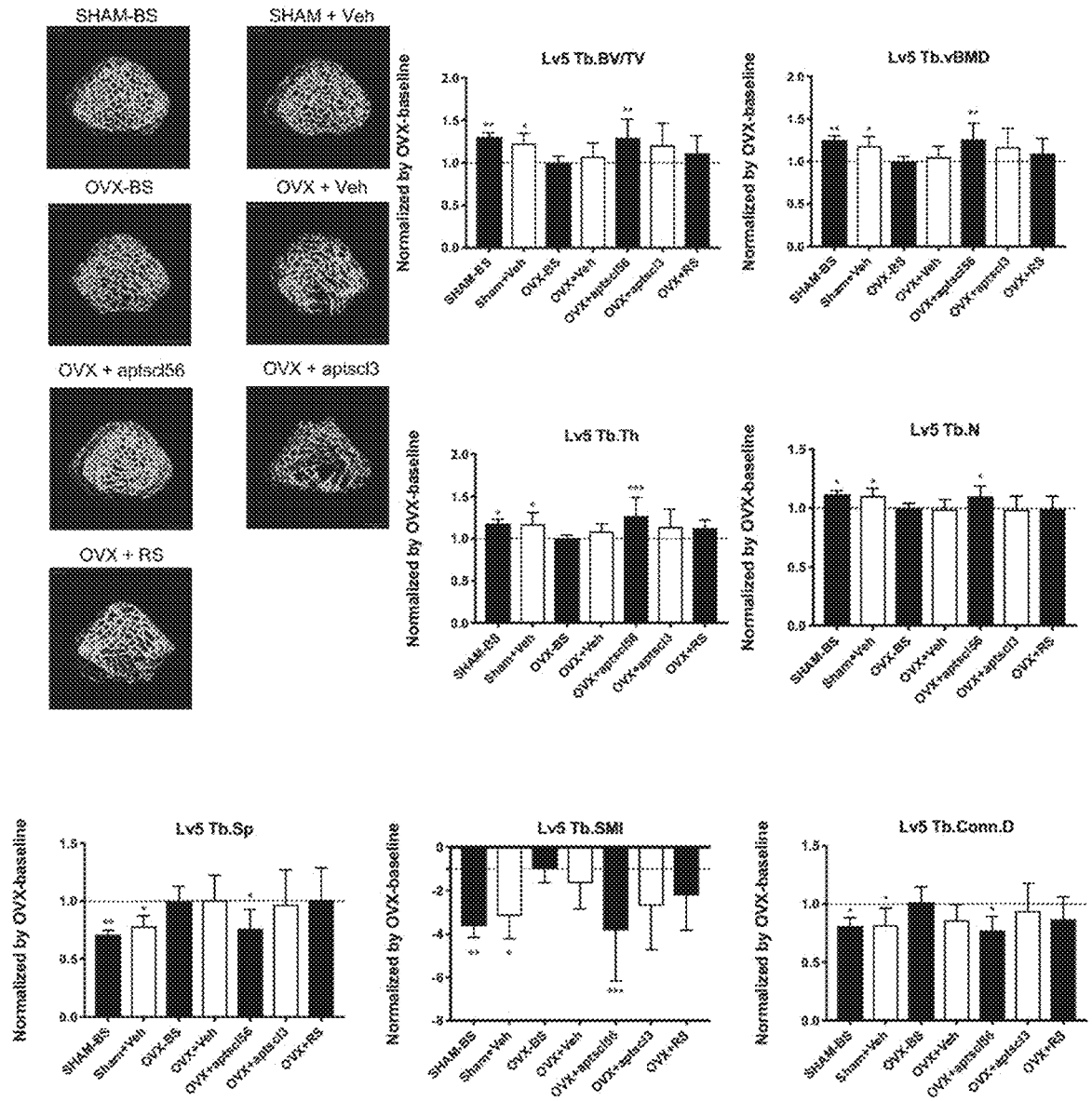

For the fifth vertebra, compared with OVX–BS, PEG40K-aptscl56 treatment for 6 weeks in OVX rats completely restored bone mass and bone structure (FIG. 13d). Compared with OVX–BS, like OVX+RS and OVX+Veh, OVX+aptscl3 did not change bone mass and bone structure.

In summary, the micro-CT data show that PEG40K-aptscl 56 can promote bone formation in OVX-induced osteoporotic rats, improve bone microstructure, and increase bone mass.

REFERENCES

Baker, M. (2015). "Reproducibility crisis: Blame it on the antibodies." Nature 521 (7552): 274-276.

Banerjee, J. (2010). "Antibodies are challenged." Indian J Med Sci 64 (3): 144-147.

Bradbury, A. and A. Pluckthun (2015). "Reproducibility: Standardize antibodies used in research." Nature 518 (7537): 27-29.

Compston, J. E. (2007). "Skeletal actions of intermittent parathyroid hormone: effects on bone remodelling and structure." Bone 40 (6): 1447-1452.

Drolet, D. W., L. Moon-McDermott and T. S. Romig (1996). "An enzyme-linked oligonucleotide assay." Nat Biotechnol 14 (8): 1021-1025.

Ellington, A. D. and J. W. Szostak (1990). "In vitro selection of RNA molecules that bind specific ligands." Nature 346 (6287): 818-822.

Engvall, E. and P. Perlmann (1971). "Enzyme-linked immunosorbent assay (ELISA). Quantitative assay of immunoglobulin G." Immunochemistry 8 (9): 871-874.

Greenspan, S. L., H. G. Bone, M. P. Ettinger, D. A. Hanley, R. Lindsay, J. R. Zanchetta, C. M. Blosch, A. L. Mathisen, S. A. Morris and T. B. Marriott (2007). "Effect of recombinant human parathyroid hormone (1-84) on vertebral fracture and bone mineral density in postmenopausal women with osteoporosis: a randomized trial." Ann Intern Med 146 (5): 326-339.

Grentzmann, G., J. A. Ingram, P. J. Kelly, R. F. Gesteland and J. F. Atkins (1998). "A dual-luciferase reporter system for studying recoding signals." RNA 4 (4): 479-486.

Groff, K., J. Brown and A. J. Clippinger (2015). "Modern Affinity Reagents: Recombinant Antibodies and Aptamers." Biotechnol Adv.

Hamersma, H., J. Gardner and P. Beighton (2003). "The natural history of sclerosteosis." Clin Genet 63 (3): 192-197.

Jayasena, S. D. (1999). "Aptamers: an emerging class of molecules that rival antibodies in diagnostics." Clin Chem 45 (9): 1628-1650.

Jellinek, D., L. S. Green, C. Bell and N. Janjic (1994). "Inhibition of receptor binding by high-affinity RNA ligands to vascular endothelial growth factor." Biochemistry 33 (34): 10450-10456.

Keefe, A. D., S. Pai and A. Ellington (2010). "Aptamers as therapeutics." Nat Rev Drug Discov 9 (7): 537-550.

McNabb, D. S., R. Reed and R. A. Marciniak (2005). "Dual luciferase assay system for rapid assessment of gene expression in Saccharomyces cerevisiae." Eukaryot Cell 4 (9): 1539-1549.

Murphy, M. B., S. T. Fuller, P. M. Richardson and S. A. Doyle (2003). "An improved method for the in vitro evolution of aptamers and applications in protein detection and purification." Nucleic Acids Res 31 (18): e110.

Ng, E. W. and A. P. Adamis (2006). "Anti-VEGF aptamer (pegaptanib) therapy for ocular vascular diseases." Ann N Y Acad Sci 1082:151-171.

Orwoll, E. S., W. H. Scheele, S. Paul, S. Adami, U. Syversen, A. Diez-Perez, J. M. Kaufman, A. D. Clancy and G. A. Gaich (2003). "The effect of teriparatide [human parathyroid hormone (1-34)] therapy on bone density in men with osteoporosis." J Bone Miner Res 18 (1): 9-17.

Padhi, D., M. Allison, A. J. Kivitz, M. J. Gutierrez, B. Stouch, C. Wang and G. Jang (2014). "Multiple doses of sclerostin antibody romosozumab in healthy men and postmenopausal women with low bone mass: a randomized, double-blind, placebo-controlled study." J Clin Pharmacol 54 (2): 168-178.

Padhi, D., G. Jang, B. Stouch, L. Fang and E. Posvar (2011). "Single-dose, placebo-controlled, randomized study of AMG 785, a sclerostin monoclonal antibody." J Bone Miner Res 26 (1): 19-26.

Pennypacker, B. L., L. T. Duong, T. E. Cusick, P. J. Masarachia, M. A. Gentile, J. Y. Gauthier, W. C. Black, B. B. Scott, R. Samadfam, S. Y. Smith and D. B. Kimmel (2011). "Cathepsin K inhibitors prevent bone loss in estrogen-deficient rabbits." J Bone Miner Res 26 (2): 252-262.

Que-Gewirth, N. S. and B. A. Sullenger (2007). "Gene therapy progress and prospects: RNA aptamers." Gene Ther 14 (4): 283-291.

Rey, J. P. and D. L. Ellies (2010). "Wnt modulators in the biotech pipeline." Dev Dyn 239 (1): 102-114.

Ruckman, J., L. S. Green, J. Beeson, S. Waugh, W. L. Gillette, D. D. Henninger, L. Claesson-Welsh and N. Janjic (1998). "2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain." J Biol Chem 273 (32): 20556-20567.

Russell, R. G., N. B. Watts, F. H. Ebetino and M. J. Rogers (2008). "Mechanisms of action of bisphosphonates: similarities and differences and their potential influence on clinical efficacy." Osteoporos Int 19 (6): 733-759.

Shum, K. T., C. Chan, C. M. Leung and J. A. Tanner (2011). "Identification of a DNA aptamer that inhibits sclerostin's antagonistic effect on Wnt signalling." Biochem J 434 (3): 493-501.

Stoltenburg, R., P. Krafcikova, V. Viglasky and B. Strehlitz (2016). "G-quadruplex aptamer targeting Protein A and its capability to detect *Staphylococcus aureus* demonstrated by ELONA." Sci Rep 6:33812.

Tuerk, C. and L. Gold (1990). "Systematic evolution of ligands by exponential enrichment: RNA ligands to bacteriophage T4 DNA polymerase." Science 249 (4968): 505-510.

van Bezooijen, R. L., J. P. Svensson, D. Eefting, A. Visser, G. van der Horst, M. Karperien, P. H. Quax, H. Vrieling, S. E. Papapoulos, P. ten Dijke and C. W. Lowik (2007). "Wnt but not BMP signaling is involved in the inhibitory action of sclerostin on BMP-stimulated bone formation." J Bone Miner Res 22 (1): 19-28.

Whitfield, J. F. (2001). "The bone growth-stimulating PTH and osteosarcoma." Medscape Womens Health 6 (5): 7.

The invention claimed is:

1. An aptamer against sclerostin, wherein the aptamer comprises a nucleotide sequence selected from the group consisting of SEQ ID NOs: 1-17 and 19-24, wherein the aptamer specifically binds to sclerostin.

2. The aptamer of claim 1, wherein the aptamer has a $K_d$ to sclerostin of less than 100 nM.

3. The aptamer of claim 1, wherein the aptamer is capable of inhibiting the biological activity of sclerostin.

4. The aptamer of claim 1, wherein the aptamer can block the antagonistic effect of sclerostin in a cell-based Wnt signaling assay.

5. The aptamer of claim 1, wherein the aptamer has an EC50 value of less than 100 μg/ml for inhibiting the antagonistic effect of sclerostin on Wnt signaling pathway.

6. The aptamer of claim 1, wherein the aptamer further comprises one or more modifications that confer enhanced nuclease resistance to the aptamer and/or enhance the in vivo half-life of the aptamer.

7. The aptamer of claim 6, wherein the modification includes a 3' inverted deoxythymidine (3' idT) modification.

8. The aptamer of claim 6, wherein the modification includes substituting one or more naturally occurring nucleotides with modified nucleotides selected from the group consisting of 2'-fluoro, 2'-methoxyethyl, 2'-methoxy or 2' allyloxy modified nucleotides.

9. The aptamer of claim 6, wherein the modification includes an internucleotide modification.

10. The aptamer of claim 6, wherein the modification includes a PEG modification, and further wherein the molecular weight of the PEG is 1 kDa to 100 kDa.

11. The aptamer of claim 6, wherein the aptamer comprises a 2'-methoxy (2'-OMe) modification, a 3' inverse deoxythymidine (3' idT) modification and/or a PEG modification.

12. A pharmaceutical composition comprising at least one aptamer against sclerostin of claim 1, and a pharmaceutically acceptable carrier or excipient.

* * * * *